(12) United States Patent
Garcia-Franco et al.

(10) Patent No.: US 7,427,506 B2
(45) Date of Patent: Sep. 23, 2008

(54) HIGH THROUGHPUT PROPERTY TESTING OF OLEFIN COPOLYMERS USING RHEOLOGICAL DETERMINATIONS

(75) Inventors: Cesar A. Garcia-Franco, Houston, TX (US); David J. Lohse, Bridgewater, NJ (US); Bruce A. Harrington, Houston, TX (US); Robert Jay Wittenbrink, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 1062 days.

(21) Appl. No.: 10/823,460

(22) Filed: Apr. 13, 2004

(65) Prior Publication Data

US 2005/0244974 A1    Nov. 3, 2005

(51) Int. Cl.
*G01N 37/00* (2006.01)
*G01N 1/00* (2006.01)
*B01L 9/00* (2006.01)

(52) U.S. Cl. .......................... 436/85; 436/174; 436/56; 422/104

(58) Field of Classification Search .................. 436/85, 436/56, 174; 422/104
See application file for complete search history.

(56) References Cited

U.S. PATENT DOCUMENTS

| | | | |
|---|---|---|---|
| 4,530,980 A | 7/1985 | Radici | |
| 5,147,936 A | 9/1992 | Peszkin et al. | |
| 5,959,297 A | 9/1999 | Weinberg et al. | |
| 6,034,775 A | 3/2000 | McFarland et al. | |
| 6,151,123 A | 11/2000 | Nielsen | |
| 6,157,449 A | 12/2000 | Hajduk | |
| 6,175,409 B1 | 1/2001 | Nielsen et al. | |
| 6,182,499 B1 | 2/2001 | McFarland et al. | |
| 6,690,179 B2 | 2/2004 | Hajduk et al. | |
| 2002/0023507 A1 | 2/2002 | Hajduk et al. | |

FOREIGN PATENT DOCUMENTS

EP    1178298    2/2002
EP    1195391    4/2002

OTHER PUBLICATIONS

XP-002302046-"Van Gurp-Palmen Plott II-Classification Of Long Chain Branched Polymers By Their Topology," Trinkle, S., et al, Rheol Acta, 2002, vol. 41, pp. 103-113.
"Rheological Characterization Of Molten Ethylene-α-olefin Copolymers Synthesized With Et[Ind]$_2$ZrCl$_2$/MAO Catalyst," Villar, M. A., et al, Polymer, Elsevier Science Publishers B.V., GB, vol. 42, No. 22, Oct. 22, 2001, pp. 9269-9279.

(Continued)

*Primary Examiner*—Jill Warden
*Assistant Examiner*—Keri A Moss

(57) ABSTRACT

A high throughput method to determine an amount of a comonomer in a copolymer sample of a copolymer system comprises the steps of providing a plurality of copolymer samples; creating an array of the copolymer samples; measuring a sample complex modulus of each of the copolymer samples at a comparison phase angle; and determining the amount of a comonomer in the copolymer sample by comparing the sample complex modulus to a calibration curve, wherein the calibration curve relates a concentration of the comonomer in the copolymer sample to a complex moduli of the copolymer sample determined at the comparison phase angle. A method of determining the amount of a comonomer in both a single copolymer sample, and in a high throughput scheme using the crossover modulus is also disclosed.

26 Claims, 12 Drawing Sheets

OTHER PUBLICATIONS

XP-002302047-"The Influence Of The Comonomer In The Copolymerization Of Ethylene With α-olefins Using $C_2H_4[Ind]_2ZrCl_2$/Methylaluminoxane As Catalyst System," Quijada, R., Macromol. Chem. Phys., vol. 197, 1996, pp. 3091-3098.

XP-002302048-"Is The Cross-Over Modulus A Reliable Measure Of Polymeric Polydispersity?," Bafna, Sudhir S., Journal Of Applied Polymer Science, vol. 63, 1997, pp. 111-113.

XP-002302049-"Well-Defined, Model Long Chain Branched Polyethylene.2. Melt Rheological Behavior," Lohse, D. J., et al, Macromolecules, vol. 35, 2002, pp. 3066-3075.

XP-0020302045-"Van Gurp-Palmen-plot: A Way To Characterize Polydispersity Of Linear Polymers," Trinkle, S., et al, Rheol Acta, vol. 40, 2001, pp. 322-328.

"Mechanical Properties Of Hydrogels And Their Experimental Determination," Anseth, Kristi S., et al, Biomaterials, Elsevier Science Publishers BV., Barking, GB, vol. 17, No. 17, pp. 1647-1657.

HIGH THROUGHPUT PROPERTY TESTING OF OLEFIN COPOLYMERS USING RHEOLOGICAL DETERMINATIONS

FIELD OF THE INVENTION

The present invention generally relates to the field of materials characterization. In particular, the invention relates to a high throughput method for evaluating mechanical or physical properties of libraries of polymers or other materials.

BACKGROUND OF THE INVENTION

Substantial research activity is being directed toward the discovery and optimization of polymeric materials for a wide range of applications. Although the chemistry of many polymers and polymerization reactions has been extensively studied, the unpredictable nature of catalysts may make prior prediction of physical or chemical properties impossible for a particular polymeric material, or a precise composition and architecture that will result from any particular synthesis scheme. Thus, characterization techniques to determine such properties may be an essential part of the discovery process.

Combinatorial chemistry refers generally to methods for synthesizing a collection of chemically diverse materials, and to methods for rapidly testing or screening this collection of materials for desirable performance characteristics, properties, and other attributes. Combinatorial chemistry approaches may greatly improve the efficiency of discovery of useful materials and processes for preparing them. In comparison to traditional materials science research, combinatorial materials research may allow for effective evaluation of much larger numbers of diverse compounds in a much shorter period of time, than may be obtained using traditional methods. However, although such high-throughput synthesis and screening methodologies are conceptually promising, substantial technical challenges exist for application thereof to specific research and commercial goals.

The characterization of polymers or other materials using combinatorial methods has only recently become known. Examples of such technology are disclosed, for example, in U.S. Pat. Nos. 6,182,499 (McFarland, et al); 6,175,409 B1 (Nielsen, et al); 6,157,449 (Hajduk); 6,151,123 (Nielsen); 6,034,775 (McFarland, et al); 5,959,297 (Weinberg, et al), and 6,690,179 (Hajduk et al.).

In order to be amenable to high throughput screening, the measured parameter or parameters must be robust and capable of being measured with precision and accuracy. Of particular interest to the present invention are combinatorial methods and apparatuses for screening polymers and other materials for physical or mechanical characteristics, and then relating those characteristics to various chemical or spatial properties.

Screening of the materials for mechanical properties presents a multitude of challenges. As an example, conventional instruments, such as conventional stress or strain testing machines and other apparatuses traditionally lack the ability to screen mechanical properties of several materials in rapid succession, in parallel, on a single substrate or a combination thereof. Thus, challenges are presented for forming systems that can quickly process and test (either in parallel or in serial succession) mechanical properties of many materials.

SUMMARY OF THE INVENTION

In one aspect of the present invention a high throughput method to determine an amount of a comonomer in a copolymer sample comprises the steps of:

a) providing a plurality of copolymer samples;
b) creating an array of the copolymer samples;
c) measuring a sample complex modulus of each of the copolymer samples at a comparison phase angle;
d) determining the amount of a comonomer in the copolymer sample by comparing the sample complex modulus to a calibration curve, wherein the calibration curve relates a concentration of the comonomer in the copolymer sample to a complex moduli of the copolymer sample determined at the comparison phase angle.

In another aspect of the present invention, a high throughput method to determine an amount of a comonomer in a copolymer sample comprises the steps of:

a) providing a plurality of copolymer samples;
b) creating an array of the copolymer samples;
c) measuring a sample crossover modulus of each of the copolymer samples at a comparison phase angle;
d) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

In still another aspect of the present invention, a method to determine an amount of a comonomer in a copolymer sample comprises the steps of:

a) providing a copolymer sample;
b) measuring a sample crossover modulus of the copolymer sample at a comparison phase angle;
c) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

DETAILED DESCRIPTION OF THE PREFERRED EMBODIMENTS

Figure 1A:
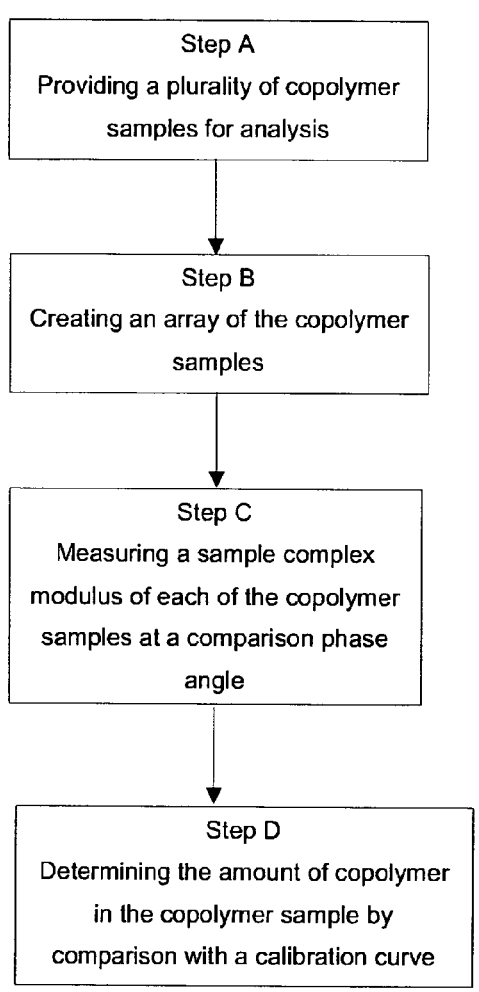
FIGS. 1a and 1b show a flowchart of possible steps for methods of the present invention.

For the purposes of this invention and the claims thereto, when a polymer is referred to as comprising an olefin, the olefin present in the polymer is the polymerized form of the olefin. The term copolymer is meant to include polymers comprising at least two monomeric species. Accordingly, a copolymer comprising polypropylene may comprise propylene having incorporated therein a single, or a plurality of other monomers within the copolymer.

A catalytically active material may be interchangeably referred to as a catalytic material, or as a catalyst. A catalyst system may comprise a catalyst, an activator when appropriate, and optionally a support. A reactor is any container(s) in which a chemical reaction occurs. In addition, the numbering scheme for the Periodic Table Groups used herein is described in CHEMICAL AND ENGINEERING NEWS, 63(5), 27 (1985). Temperatures are listed in degrees Celsius (° C.) unless otherwise noted.

By branched olefinic monomer, it is meant a non-linear monomer component comprising a carbon-carbon double bond. Accordingly, branched olefinic monomers include non-linear alpha olefins, cyclic olefins, aromatic olefins, substituted aromatic olefins, and the like, which are further described herein.

Further, for purposes of this invention, Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, TMS is trimethylsilyl, a per fluoro radical is an organic radical having one or more available hydrogen atoms substituted with fluorine atoms.

A mixture may refer to a collection of molecules, ions, electrons, chemical substances, and the like. Each component in the mixture can be independently varied. A mixture can consist of two or more substances intermingled with no constant percentage composition, wherein each component may or may not retain its essential original properties, and where molecular phase mixing may or may not occur. In mixtures, the components making up the mixture may or may not remain distinguishable from each other by virtue of their chemical structure.

These and other aspects of the invention are to be considered exemplary and non-limiting, and are discussed in greater detail below. The several aspects of the characterization instruments and methods disclosed and claimed herein can be advantageously employed separately, or in combination to efficiently characterize a variety of materials, with particular emphasis on solid materials and polymeric materials.

In preferred embodiments, these features are employed in combination to form a materials characterization system that can operate as a high-throughput screen in an industrial production scheme, and/or in a combinatorial materials science research program directed to identifying and optimizing new materials. Such materials appropriate for combinatorial research may include, for instance, polymers, catalysts, products of various polymerization reaction conditions, lubricants, gels, adhesives, coatings and/or products of new post-synthesis processing conditions. Other materials appropriate for combinatorial research according to the present invention may include, but are not limited to, foodstuffs, cosmetics, beverages, lotions, creams, pharmaceuticals, inks, body fluids, fuels, additives, detergents, surfactants, shampoos, conditioners, dyes, waxes, electrolytes, fuel cell electrolytes, photoresist, semiconductor material, wire coatings, hair styling products and the like.

Rheological Evaluation of Copolymers

A key goal of polymer science has been to relate the chemical structure of macromolecules to their basic physical properties. The packing length model has proved successful at predicting the degree of entanglement of flexible polymers based on their chain dimensions and density (Fetters, et al. Macromolecules 27, 4639-4647, 1994). This model has recently been extended further for polyolefins by connecting their chemical architecture to the packing length and so to the plateau modulus (Fetters et al. Macromolecules 35, 10096-10101, 2002).

The simplest model for the packing length of polyolefin chains is the backbone equivalence model, which states that the size of a coil is determined just by the contour length of the backbone. This is the same as assuming that the ratio of trans to gauche configurations is the same for all polyolefins as it is for polyethylene. For the plateau modulus this leads to the following prediction:

$$G_N^o = \left(\frac{14}{m_b}\right)^3 (G_N^o)_{PE} \qquad \text{(Eq. 1)}$$

where $m_b$ is the molecular weight per backbone bond and $(G_N^o)_{PE}$ is the plateau modulus of polyethylene.

However, it has been shown that the backbone equivalence model, while capturing the qualitative drop of $G_N^o$ with increasing comonomer content and length, may not predict the plateau modulus quantitatively. By fitting the data on polyolefins, the following equations have been derived, which depend on the value of $m_b$:

$$G_N^o = 24820 m_b^{-3.49} \quad (m_b = 14\text{-}28 \text{ g/mol}) \qquad \text{(Eq. 2a)}$$

and $$G_N^o = 41.84 m_b^{-1.58} \quad (m_b = 35\text{-}56 \text{ g/mol}) \qquad \text{(Eq. 2b)}$$

The physics behind these relations are not well understood, beyond indicating that the gauche/trans ratio depends on $m_b$. However, as disclosed herein, it has been unexpectedly discovered that this model holds up over a broad range of polymer composition. The results disclosed herein clearly show the strong effect of comonomer content on plateau modulus, in contrast to the views expressed by some in the literature (Wood-Adams et al. Macromolecules 33, 7489-7499, 2000).

Measurement and Calculation of the Plateau Modulus, $G_N^o$

One viscoelastic material functions is the modulus associated with the rubbery plateau, $G_N^o$, exhibited by polymer melts. According to the theory of rubber elasticity, the plateau modulus is defined by the following equation $$G_N^o = \frac{\beta \rho R T}{M_e} \quad \text{(Eq. 3)}$$

where R is the gas constant, T the absolute temperature, and β a numerical coefficient that is equal to about 1 to about ⅘ (See Larson et al. J. Rheol 47:809-818, 2003) for a discussion relating to the value of β).

$G_N^o$ may relate to polymer physics as a direct way to measure the degree of entanglement in a polymer melt through Eq. 3. The behavior of polymer melts in both the rubbery and terminal zones is strongly affected by $M_e$, and it may have consequences on both viscous and elastic properties. $M_e$ may also affect the micromechanisms of deformation (crazing and shear yielding) and the failure of polymers in the solid state.

Methods useful to calculate $G_N^o$ from rheological data include integration of the G"(ω) vs. ω dispersion. This method is predicated on the integration of the loss modulus, G"(ω) in the terminal zone according to the following equation:

$$G_N^o = \left(\frac{2}{\pi}\right) \int_{-\infty}^{\infty} G''(\omega) \, d\ln\omega \quad \text{(Eq. 4)}$$

However, care may be needed when using this equation as it may be necessary to separate the contribution of the terminal zone from the rest of the relaxation spectrum, and sometimes this may be difficult if not impossible. A variation of this method may also be used whereby the integration of the G"-ω dispersion is carried out from −∞ to the frequency at which G" exhibits a maximum, $\omega_{max}$, and multiplying the result by two:

$$G_N^o = \left(\frac{4}{\pi}\right) \int_{-\infty}^{\omega_{max}} G''(\omega) \, d\ln\omega \quad \text{(Eq. 5)}$$

This method assumes that the dispersion is symmetric.

Marvin and Oser (J. Res. Natl Bur Stand 66B(4):171-180, 1963), proposed a molecular model representing the mechanical response of a rubberlike polymer including entanglement effects. Their model proposes the following relationship between the plateau modulus, $G_N^o$, and the value of the loss modulus, G", at its maximum:

$$G_N^o = 4.83 G''(\omega)_{max} \quad \text{(Eq. 6)}$$

It is well known that the crossover parameters which describe the frequency and modulus at the point at which G' is equal to G" have been correlated to $M_w$ and the molecular weight distribution, MWD. The frequency at the crossover, $\omega_{co}$, moves to higher frequency with decreasing $M_w$, and increasing temperature, whereas the crossover modulus, $G_{co}$, strongly depends on the MWD and shows only a weak temperature dependence. As the MWD broadens, $G_{co}$ decreases. The effect of the molecular weight and temperature on the dynamic moduli is to move them along the frequency axis, whereas the effect of the MWD moves the moduli along the vertical axis.

Accordingly, for polydisperse materials having $M_w/M_n <$ ca. 3, the ratio $G_N^o/G_{co}$ may be relatively insensitive to the shape of molecular weight distribution curves. Thus, it can be given as a function of the polydispersity ratio $M_w/M_n$ as follows $$\log\left(\frac{G_N^o}{G_{co}}\right) = 0.38 + \frac{2.63 \log\left(\frac{M_w}{M_n}\right)}{1 + 2.45 \log\left(\frac{M_w}{M_n}\right)} \quad \text{(Eq. 7)}$$

This relation may be verified both theoretically using lognormal and Schulz-Flory distributions, and also experimentally using a number of amorphous polymers for which $G_{co}$ and $G_N^o$ can be simultaneously determined as a function of $M_w/M_n$.

In addition, using the double reptation mixing rule and the Generalized Exponential Function (GEX) to describe the MWD may essentially expand equation (Eq. 7) by including higher moments of the MWD:

$$\log\left(\frac{G_{co}}{G_N^o}\right) = \frac{-0.524 + 0.34 \log \frac{M_w}{M_n} - 1.843 \log \frac{M_z}{M_w}}{1 - 0.559 \log \frac{M_w}{M_n} + 0.841 \log \frac{M_z}{M_w}} \quad \text{(Eq. 8)}$$

Since $\omega_{co}$ and $G_{co}$ are well resolved experimental parameters, an alternative to the integration of the G"-ω dispersion may be used in the frame of the GEX model to calculate $G_N^o$:

$$\gamma G_N^o = \frac{4}{\pi} \int_0^{\omega_{co}} G'' \, d\ln\omega \quad \text{(Eq. 9)}$$

where $0 < \gamma < 1$. Although γ depends on the MWD shape, the following working approximation may be given by:

$$\log\gamma = (0.0103 - 0.478 L_1 + 0.603 L_1^2 - 1.02 L_2 + 1.47 L_2^2 - 1.61 L_1 L_2) \quad \text{(Eq. 10)}$$

where $L_1 = \log(M_w/M_n)$ and $L_2 = \log(M_z/M_w)$. Accordingly, equations (8) and (9) may give essentially the same results.

The plateau modulus and the entanglement molecular weight of a copolymer may thus obey a geometric mean relationship with respect to composition:

$$\log(G_N^o) = \Sigma \phi_j \log G_{Nj}^o$$

$$\log M_e = \Sigma \phi_j \log M_{ej} \quad \text{(Eq. 11)}$$

where $\phi_j$ the volume fraction of comonomer j, $G_{Nj}^o$ the plateau modulus for the homopolymer of j and $M_{ej}$ its entanglement molecular weight. As disclosed herein, it may thus be possible to derive similar mixing rules expressed in terms of weight fraction rather than volume fraction.

Recently Van Gurp and Palmen (Proc. XII Int. Congr. On Rheology, Quebec City (Quebec), Canada: 134-135 (1996), and Rheology Bulletin 67, 5-8 (1998)) presented an approach to verify the validity of the time-temperature superposition principle (tTSP). In this method, the phase angle, δ (=atan (G"/G')) of the measured dynamic rheological data, also referred to herein as a comparison phase angle, may be plotted against the corresponding absolute value of the shear complex modulus, |G*|, also referred to herein as simply as a complex modulus. In such a representation isothermal frequency curves merge into a common line if tTSP holds. It may thus be argued that this verification of tTSP for a given polymeric melt is predicated on the exclusion of the temperature dependent characteristic time, $\lambda_o$, as well as those properties based on such characteristic time according to the Doi-Edwards scaling laws.

Various polymers have thus be studied in an effort to establish the van Gurp-Palmen plots as a useful and reliable tool for the rheological characterization of polymer melts. These included linear monodisperse anionically polymerized polystyrenes, and polymethylmethacrylates, and some metallocene polyolefins: polyethylene, polypropylenes of varying tacticity, polybutene, and ethylene/propylene copolymers, wherein a linearity between log |G*| values at any given $\delta$ and composition expressed in wt % has been observed. Accordingly, a nearly linear relationship between log |G*| at a given $\delta$ as a function of composition may be useful in determining chemical properties of various copolymers. However, in various polymers (e.g., linear monodispersed polystyrene) it has been observed that the evolution of $\delta$ as a function of |G*| depended on molecular weight, which is at odds with linear hydrogenated polybutadienes, which has shown molecular weight invariance in the van Gurp-Palmen plot.

Figure 3:
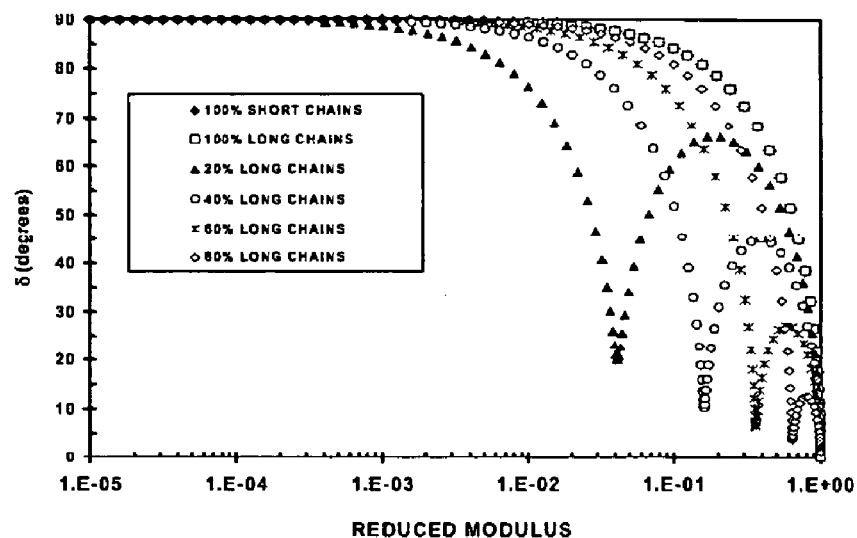
FIG. 3 shows double reptation modeling of linear binary blends of various polymeric chains.

The van Gurp-Palmen plots of linear polymers may be predicted by calculating the dynamic moduli using double reptation mixing rules. The van Gurp-Palmen representation of the linear viscoelastic data may thus be molecular weight independent. As shown in FIG. 3, it has thus been discovered herein that the relaxation regions corresponding to populations may be evident in such data, and thus as the amount of long chain branches increases in a blend, the relaxation zone corresponding to the short branches decreases and moves to higher values of the reduced complex modulus ($|G^*|/G_N^o$).

This observation becomes particularly relevant with respect to the so-called modified Cole-Cole plots (see Harrel and Nakajima, J. Applied Polym Sci 29:995-1010(1984)) which are constructed by plotting the loss modulus, $G''(\omega)$ against the storage modulus $G'(\omega)$ in log-log coordinates. This is in contrast to the classical Cole-Cole plot where the imaginary component, $\eta''(\omega)$ of the complex viscosity is plotted against the real part $\eta'(\omega)$ of the complex viscosity, $\eta^*(\omega)$, in linear coordinates. These modified Cole-Cole plots thus provide a molecular weight and temperature independent representation of the linear viscoelastic properties. They have been used for characterizing MWD and long chain branching effects, in elastomers and in order-disorder transition temperatures of block copolymers. It has also been discovered that in the terminal region, log G'' for monodisperse flexible polymer chains is proportional to log G', with a slope of ½, independent of the molecular weight, and temperature has a very weak effect on log G'' versus log G' plots.

The modified Cole-Cole plots may thus be useful as a way to extract the crossover parameters, $\omega_{co}$ and $G_{co}$. As $M_w$ increases and the temperature decreases, $\omega_{co}$ moves to lower frequency. On the other hand, $G_{co}$ depends mostly on the molecular weight distribution. As MWD narrows, the crossover modulus may also increase. The viscoelastic properties of narrowly distributed linear metallocene catalyzed poly (ethylene-co-styrene) copolymers (styrene content varied from 0 to 20.5 mol %) have been studied and the following expression proposed to calculate an approximation to the plateau modulus:

$$G_N^o \approx \frac{\eta_o}{\lambda_{co}} \quad \text{(Eq. 12)}$$

where $\eta_o$ is the zero shear viscosity and $\lambda_{co}$ is a characteristic time (an approximation to the terminal relaxation time) given by the reciprocal of $\omega_{co}$.

In the present invention, the practical importance of this subject thus may become evident since the stiffness of typical crystalline engineering thermoplastics at room temperature may be about ⅓ to ⅕ that of the same material at low temperatures. The stiffness of a semicrystalline polymer may thus vary with temperature by more than a factor of 10 between low temperatures and temperatures of common use. The fundamental viscoelastic properties measured by DMTA include the dynamic storage modulus E', the dynamic loss modulus, E'', and the damping factor given by the tangent of the loss angle, tan $\delta(=E''/E')$. The dynamic storage modulus, E', has been found to agree with the flexural modulus measured according to ASTM D 790 protocol.

The drop of the stiffness or modulus vs. temperature may then occur in certain temperature intervals, each associated with an anelastic relaxation process that arise as a consequence of various types of molecular motions. Polymers that crystallize very rapidly to high degrees of crystallinity such as polyethylene may thus show at least three relaxation processes. These are referred to herein as the $\alpha$-, $\beta$, and $\gamma$-relaxations in descending order with temperature.

The $\alpha$-relaxation may occur due to the motion of —CH$_2$— units of polyethylene in the crystalline lattice. The $\alpha$-relaxation may be ascribed to vibrational or reorientational motions within the crystals, and/or it may be considered that the amorphous phase is also involved in this relaxation. It has also been observed that in mechanical relaxations of single polyethylene crystals, $\alpha$-relaxation may be due to the motion of the chain folds at the crystal surfaces. The $\alpha$-relaxation may also be due to two overlapping relaxations with different activation energies, as the $\alpha$-relaxation shows a strong dependence on the degree of crystallinity. In general, linear polyethylenes with a high degree of crystallinity may show a strong $\alpha$-relaxation. Ethylene homopolymers show a large peak spanning between 0 and 100° C. In the case of ethylene copolymers, the $\alpha$-transition tends to decrease or even to disappear as the comonomer content increases. The $\alpha$-transition temperature may also depend on the side-branch content, crystallization method, and perhaps the mechanism of recrystallization.

The $\beta$-relaxation may be presumed to be the glass-rubber relaxation process in the residual uncrystallized amorphous fraction. The $\beta$-relaxation may not be prominent in comparison to the $\alpha$- and $\gamma$-relaxations for linear polyethylenes. Accordingly, the question of the actual existence may be present, which may lead to assignment of the more prominent $\gamma$-process to be the glass transition in the amorphous phase. The $\beta$-relaxation has been detected in ethylene copolymers and branched polyethylenes at temperatures ranging from −75° C. to 25° C., but scarcely appears in linear polyethylene.

The $\beta$-relaxation may thus result from motions of chain units in the interfacial region. The intensity of this transition may be related to the branch level and to the degree of crystallinity, since it may increase as the comonomer content increases in a particular ethylene copolymer. $^{13}$C NMR resonance however, may allow for the conclusion that the $\beta$-relaxation is related to the segmental motions of disordered chains located in the interfacial region and it is not associated with motions of an unrestrained and completely amorphous polymer (see Decgter et al., J. Polym. Sci. Polym Phys Ed 20:641-650 (1982)).

The γ-relaxation may involve the amorphous fraction, and thus may be associated with a single relaxation process predominantly of amorphous origin. A partial origin in the crystalline phase may also follow. For linear polyethylene, it may be concluded that the γ-relaxation is entirely of amorphous phase origin. This relaxation may typically be of the joint movements of chains containing three or more methylene units in the main chain. The γ-relaxation occurs at temperatures below −100° C. and it is normally attributed to the motion of —$CH_2$— units in the amorphous region.

EXAMPLES

Copolymer Synthesis

A series of ethylene-octene copolymerizations were carried out in a single-phase, liquid-filled, stirred-tank reactor with continuous flow of feeds and continuous withdrawal of products under equilibrium conditions. All polymerizations were done in a hexanes solvent system, using soluble, single-sited, ansa-metallocene catalyst and soluble, discrete, non-coordinating borate anions as co-catalyst. A homogeneous dilute solution of tri-n-octylaluminum in hexane was used as a scavenger in the minimum allowable concentration needed to maintain reaction. The polymerizations were carried out at reasonably low temperatures using hydrogen to control molecular weight. In this manner it was possible to minimize mis-insertions and macromer re-insertion that can contribute to long chain branching. This combination of a single-phase, homogeneous, continuous, solution process at lower temperatures helped to ensure that the products were as linear as possible and that products properties were as narrowly disperse as possible using metallocene catalyst.

Hexanes and toluene (used for preparing metallocene catalyst and co-catalyst solutions) were purified over beds of 3 A mole sieves and basic alumina. Ethylene and octene were dried over beds of 3 A mole sieves only. Hydrogen was used as received without further purification. Most feeds were pumped into the reactors using metering pumps. Ethylene and hydrogen flowed as a gas through a mass flow meter/controller. Reactor temperature was controlled either by circulating water through a reactor cooling jacket, or adiabatically, by controlled chilling of the feeds and using the heat of polymerization to heat the reactor. Reactor temperatures were generally kept around 50 to 70° C.

The reactors were maintained at a pressure in excess of the vapor pressure of the reactant mixture to keep the reactants in the liquid phase. In this manner the reactors were operated liquid full with a homogeneous single phase. Ethylene and octene feeds were combined into one stream and then mixed with a prechilled hexanes stream. A dilute hexane solution of a tri-n-octylaluminum scavenger was added to the combined solvent and monomer stream just before it entered the reactor to further reduce the concentration of any catalyst poisons. A mixture of the catalyst components in toluene or a toluene/solvent mixture was pumped separately to the reactor and entered through a separate port. The product of the reactor exited through a pressure control valve set to an appropriate pressure.

The reaction mixture was stirred aggressively using a magna-drive system with three directionally opposed tilt paddle stirrers set to about 750 rpm. Previous experiments have shown that thorough mixing is achieved with this system over a broad range of solution viscosities. Flow rates were set to maintain an average residence time in the reactor of about 10 minutes.

On exiting the reactor the reaction mixture pressure for the lab scale samples was reduced to atmospheric pressure. Unconverted monomers in the solution were flashed off into the vapor phase in a vapor-liquid separator. The liquid phase, containing mainly hexanes and dissolved copolymer, was collected into a can containing isopropanol for quench. The copolymer was recovered from solution by solvent evaporation under heat and vacuum.

Using the processes described above, a series of ethylene-octene polymerizations were carried out according to the following general procedure:

Example 1

Catalyst Activation

μ-(p-$Et_3SiPh)_2$C(Cp)(2,7di-t-BuFlu)$HfMe_2$ (A1, 82.5 mg, 0.0872 mmole), was pre-activated with N,N'-dimethylanilinium tetrakis (perfluorophenyl) borate [$DMAH^+$ $B(pfp)_4$] (B1, 67.5 mg, 0.0843 mmole), in toluene (900 mL) under an inert atmosphere. This mixture was allowed to activate until the evolution of methane stopped and the solution was clear (~5 min.), and then sealed with nitrogen pressure for transfer to a delivery vessel. The catalyst solution was pumped to the reactor from the delivery vessel at a controlled rate using a calibrated HPLC pump.

Copolymer Synthesis

A mixture of chilled hexanes (5.4 L/h) was pumped into a 1 liter, liquid filled, stirred tank reactor while the reactor temperature was held constant using a steam/water mixture flowing through the reactor jacket. The pre-activated A1 catalyst in toluene (0.075 L/h, 0.0073 mmole/h) and a scavenger solution of tri-n-octylaluminum in hexane (0.090 L/h, 0.3226 mmole/h) were then pumped to the reactor for 20 min. before monomers were introduced. 1-Octene (0.660 L/h, 4.21 mole/h) was pumped to the chilled feed line as a liquid. Ethylene was delivered as a gas in a controlled fashion through a mass flow meter/controller (120.0 g/h, 4.286 mole/h) and dissolved in the chilled solvent before entering the reactor. Hydrogen gas was delivered to the chilled feed line in a controlled manner through a mass flow meter/controller (0.0096 g/h, 80.4 ppmw on ethylene) as needed for molecular weight control. Continuous flow was established at a constant temperature (50° C.) and stirring rate (~1550 rpm). Onset of polymerization activity was determined by an observation of a viscous product and reduced steam heat needed to control reactor temperature. Once activity was established, one hour was provided to establish equilibrium conditions. The resulting mixture, containing mostly solvent, polymer (5.5 wt %), and unreacted monomers was collected (0.5 h) in a can containing an alcohol to quench the polymerization activity. A stabilizer was added to the polymer solution and mixed. The solvent was evaporated on a steam bath and the product dried under vacuum at 90° C. for 16 h.

An array of samples were produced having a varying amount of copolymer, as is indicated by the sample name (e.g., In the polymer name in Table I the EO stands for ethylene octene and the number stands for the approximate comonomer content.) A summary of these data is presented in Table I.

TABLE I

Molecular Characterization of Ethylene-Octene Copolymers

| Polymer | Octene Content (wt %)[a] | Octene Content (mole %) | $CH_3/1000\ C$[b] | $\rho$ (g/cc)[c] | $M_w$[d] (kg/mol) | $M_w/M_n$[e] | $M_z/M_w$[d] |
|---|---|---|---|---|---|---|---|
| EO19 | 19.0[a] | 5.6 | 24.0 | 0.904 | 81.9 | 2.05 | 1.54 |
| EO30 | 29.8[a] | 9.6 | 37.3 | 0.885 | 129. | 1.95 | 1.48 |
| EO38 | 3.75[a] | 13.0 | 46.8 | 0.870 | 173. | 1.99 | 1.47 |
| EO44 | 43.5 | 16.2 | 54.5 | 0.856 | 197. | 2.01 | 1.51 |
| EO52 | 52.4 | 21.6 | 65.5 | 0.853 | 233. | 2.01 | 1.50 |
| EO56 | 56.2 | 24.3 | 70.3 | 0.854 | 285. | 2.10 | 1.48 |
| EO70 | 70.3 | 37.2 | 87.9 | 0.853 | 941. | 1.95 | 1.39 |
| EO87 | 87.4 | 63.4 | 109. | 0.852 | 1270 | 1.96 | 1.36 |
| EO92 | 92.3 | 75.1 | 115. | 0.851 | 1080 | 1.94 | 1.37 |

[a]Calculated from an FTIR correlation based on CNMR Standards. Otherwise calculated directly from $^{13}$CNMR.

[b]Calculated from $\dfrac{CH_3}{1000\ C} = \dfrac{C_M}{0.2 + (0.001)(6)C_M}$ where $C_M$ stands for % molar octene content. (Krentsel BA et al. 1997)
[c]Calculated from a refractive index correlation based on ASTM density standards.
[d]Low angle laser light scattering
[e]Differential refractive index Small amplitude oscillatory shear experiments were then employed to measure the linear viscoelastic properties of these copolymers. All dynamic Theological experiments were performed using a strain-controlled instrument ARES (Advanced Rheometrics Expansion System—Rheometrics Scientific) with parallel plates (25 mm diameter) geometry. To minimize thermally induced chemical changes the experimental specimens were kept in a nitrogen atmosphere during the rheological test. The experimental specimens were stabilized and compression molded at 190° C., at a diameter of 25 mm and a thickness of approximately 1 mm. Because of limited amount of copolymer available for rheological testing, the experiments were carried on a single specimen using the thermal expansion coefficient (2.813 μm/° C.) of the tools to set the gap at different temperatures. The time-temperature superposition principle [Ferry 1980] was used to reduce the data (master curve) at 190° C.

Dynamic mechanical experiments were also carried out on a Rheometrics Solid Analyzer-II (Rheometrics Scientific Inc). The samples were compression molded at 190° C. to obtain experimental specimens with uniform thickness (0.2-0.5 mm) and allowed to cool at room temperature. Rectangular specimens averaging 23 mm long and 6.42 mm wide were used. The experiments were carried out in the tensile mode at 1 Hz from, heating rate of 2° C./min from −150° C. to the melting point.

The dynamic data from the master curves at 190° C. were employed to calculate $G_N^o$ of these ethylene/octene copolymers. The rubbery plateau modulus was calculated using the three methods outlined earlier (Eqs. 4, 6, 7, and 8). The integration of the loss modulus-frequency dispersion was achieved by fitting the experimental results with a Gauss function followed by the formal integration. A summary of the plateau modulus calculated by these four different methods is given in Table II.

TABLE II

Rheological Parameters of Ethylene-Octene Copolymers

| Polymer | $G_N^o$ (MPa)[a] | $G_N^o$ (MPa)[b] | $G_N^o$ (MPa)[c] | $G_N^o$ (MPa)[d] | $\lambda_{co}$ (s) | $G_{co}$ (MPa) |
|---|---|---|---|---|---|---|
| EO30 | 1.27 | 1.43 | 1.00 | 0.84 | 0.0079 | 0.149 |
| EO38 | 0.81 | 0.91 | 0.85 | 0.70 | 0.02 | 0.125 |
| EO44 | 0.79 | 0.76 | 0.62 | 0.52 | 0.022 | 0.090 |
| EO52 | 0.57 | 0.57 | 0.50 | 0.42 | 0.029 | 0.072 |
| EO56 | 0.47 | 0.45 | 0.40 | 0.32 | 0.039 | 0.057 |
| EO70 | 0.25 | 0.24 | 0.23 | 0.18 | 0.65 | 0.035 |
| EO87 | 0.13 | 0.12 | 0.12 | 0.090 | 0.62 | 0.018 |
| EO92 | 0.090 | 0.096 | 0.084 | 0.063 | 0.27 | 0.013 |

[a]See Equation (4)
[b]See Equation (6)
[c]See Equation (7)
[d]See Equation (8)

Figure 4:
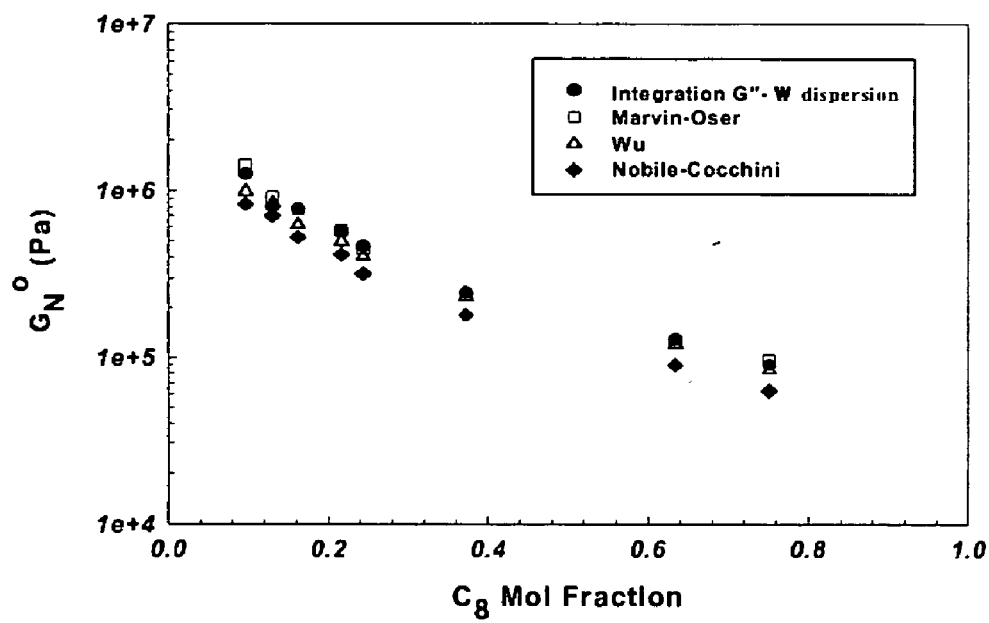
FIG. 4 shows a rubbery plateau modulus of EO copolymers calculated by four different methods, plotted against copolymer composition expressed in terms of comonomer mole fraction.
Figure 5:
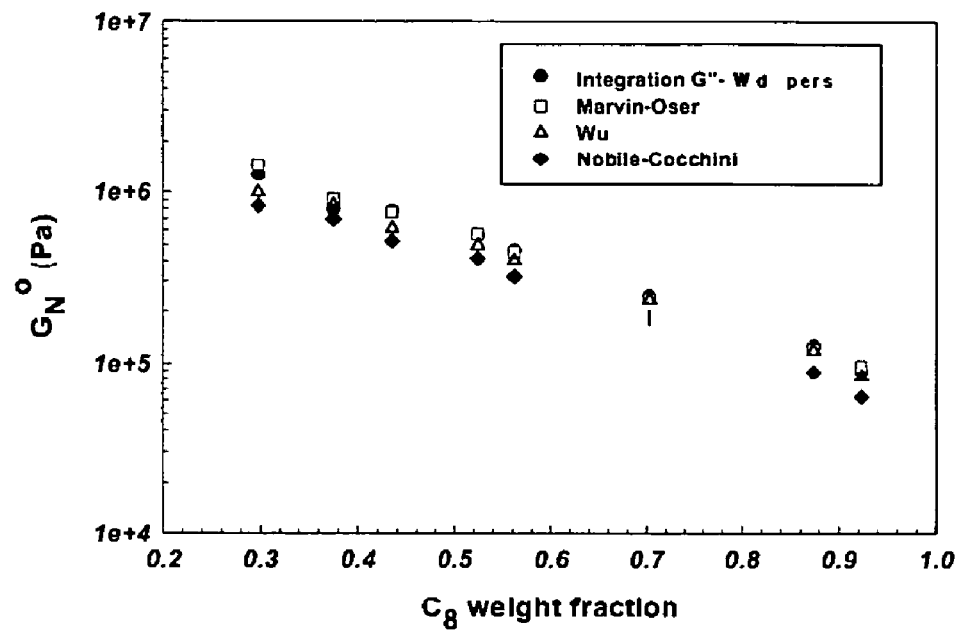
FIG. 5 shows a rubbery plateau modulus of the EO copolymers calculated by four different methods, plotted against copolymer composition expressed in terms of comonomer weight fraction.

FIG. 4 shows the values of the plateau modulus calculated by these four methods as a function of the octene mol fraction, while FIG. 5 shows these values of $G_N^o$ against the octene weight fraction. These results show the strong effect that comonomer content has on the degree of entanglement, in contrast to opinions expressed by others, and reflect an acceptable agreement of the values of $G_N^o$ obtained with the integration of the G"-ω dispersion, the Marvin-Oser theory's result, and Wu's model (see J. Polymer Sci, Polym Phys Ed 27:723-741). However, the results obtained using the Cocchini and Nobile (Rheol Acta 42:232-242(2003)) equation are unexpectedly and significantly lower than those from the other three methods. For this reason, in the following the values of $G_N^o$ calculated by the quadrature of the loss modulus-frequency dispersion were used.

Figure 6:
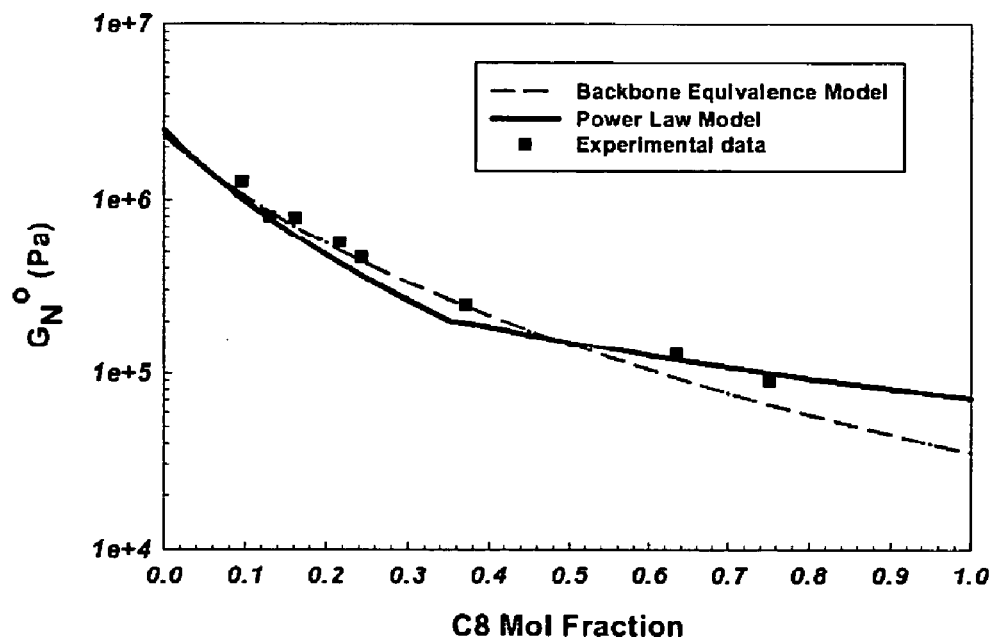
FIG. 6 shows a comparison of the experimental values of the rubbery plateau modulus with the predictions of the backbone equivalence (Eq. 1) and power law (Eq. 2) models.

FIG. 6 shows the predictions of the backbone equivalence model (Eq. 1) and power law model (Eq. 2) along with the experimental results of these ethylene/octene copolymers. The results reflect a good agreement between the experimental values and those predicted by the power law model. Thus, the rheological behavior of ethylene-octene copolymers fits into the general pattern shown by nearly all polyolefins.

Figure 7:
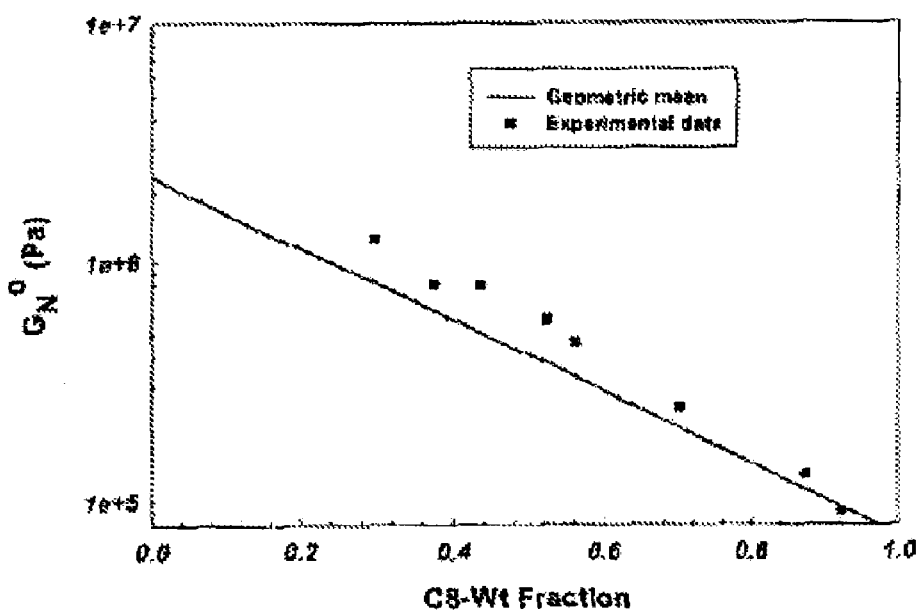
FIG. 7 shows a comparison of the experimental values of the rubbery plateau modulus with the geometric mean model (Eq. 11)

FIG. 7 shows the plateau moduli of the ethylene-octene copolymers vs. the prediction of the geometric mean mixing rule (Eq. 11) using $G_N^o$ for PE as 2.3 MPa and that of polyoctene as 0.072 MPa. It has been discovered that the geometric mean relationship underestimates the values of the ethylene-octene copolymer plateau modulus substantially.

Figure 8:
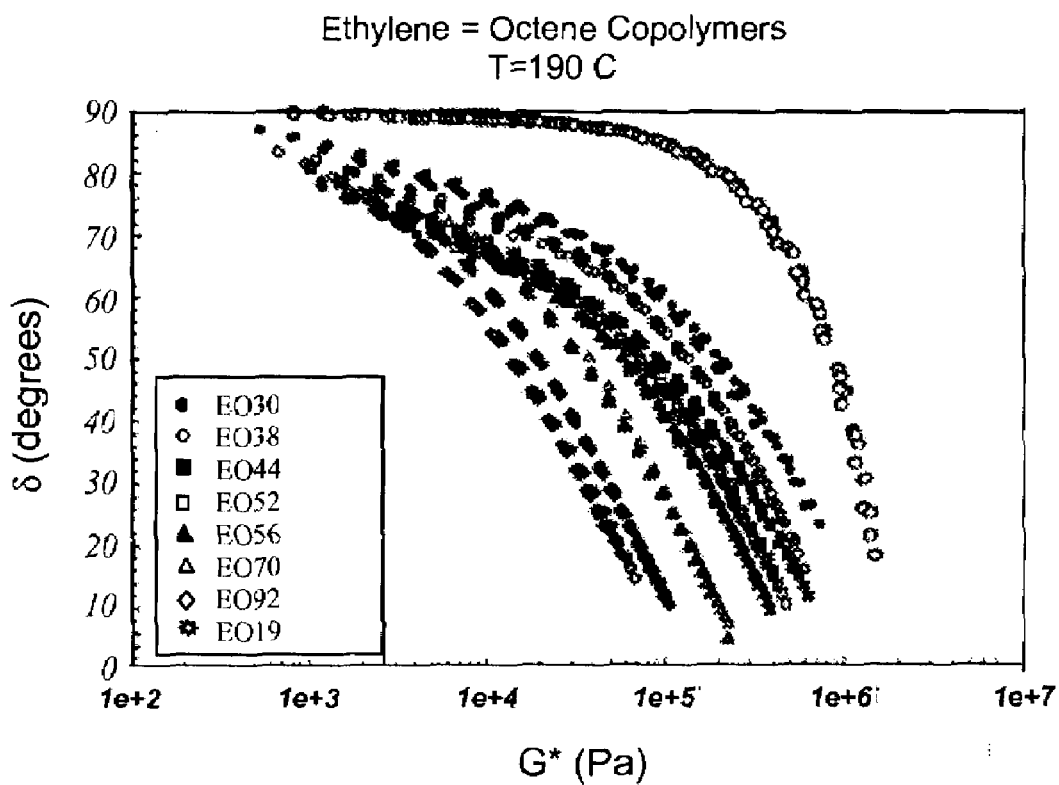
FIG. 8 shows a Van Gurp-Palmen plots of EO copolymers; linear monodisperse hydrogenated polybutadiene PEL123, (Comparative Example 1) included as reference.

FIG. 8 shows the van Gurp-Palmen plots of these ethylene-octene copolymers based on the master curves data at 190° C. Notice that FIG. 8 also shows the evolution of δ in terms of |G*| of a linear monodisperse hydrogenated polybutadiene PEL 123 (Comparative Example 1). This representation of the linear viscoelastic properties is molecular weight and temperature invariant; however, it is very sensitive to polydispersity and the presence of long chain branching. In the present case, δ shows a strong dependence on the comonomer amount. As octene content increases, the entire curve shifts towards the left on the modulus axis. The value of $G_N^o$ is approximated by these curves at the lower limit of δ and could be estimated by extrapolation.

Figure 9:
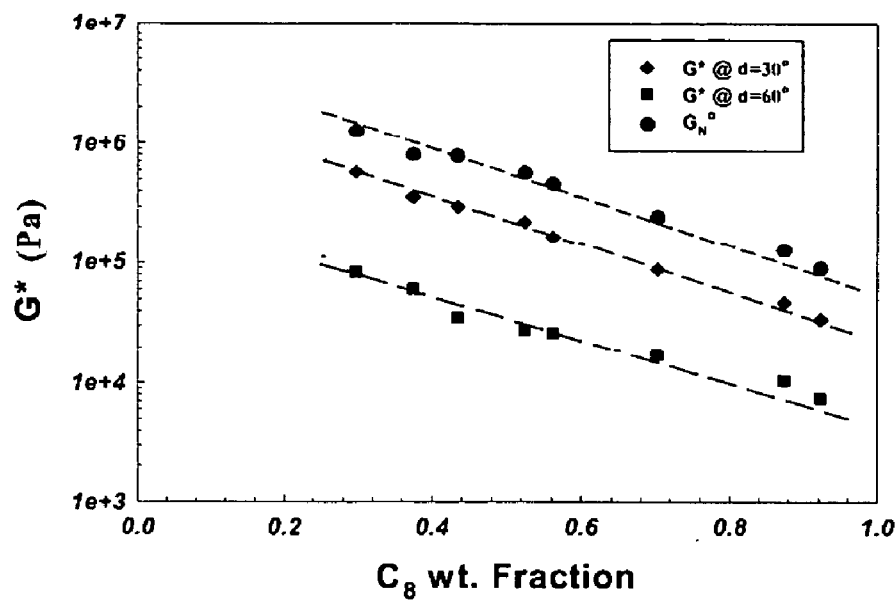
FIG. 9 shows $|G^*|$ measured at given values of $\delta$, vs. copolymer composition.

FIG. 9 shows the quantitative correlation of rheological performance with composition, the values of |G*| at δ=30° and 60° were plotted, as well as $G_N^o$, against the octene weight fraction. Thus in the present invention, it is possible to obtains a nearly linear relationship between log |G*| and composition. Thus, the van Gurp-Palmen plot may be used, as disclosed herein, at a phase angle, referred to herein as a comparison phase angle, of from about 5° to about 85°, preferably at a comparison phase angle of about 20° to about 60°, more preferably at a comparison phase angle of about 30° to about 40°. Accordingly, the comparison phase angle may be in a region closer to plateau modulus than to the terminal region.

Figure 10:
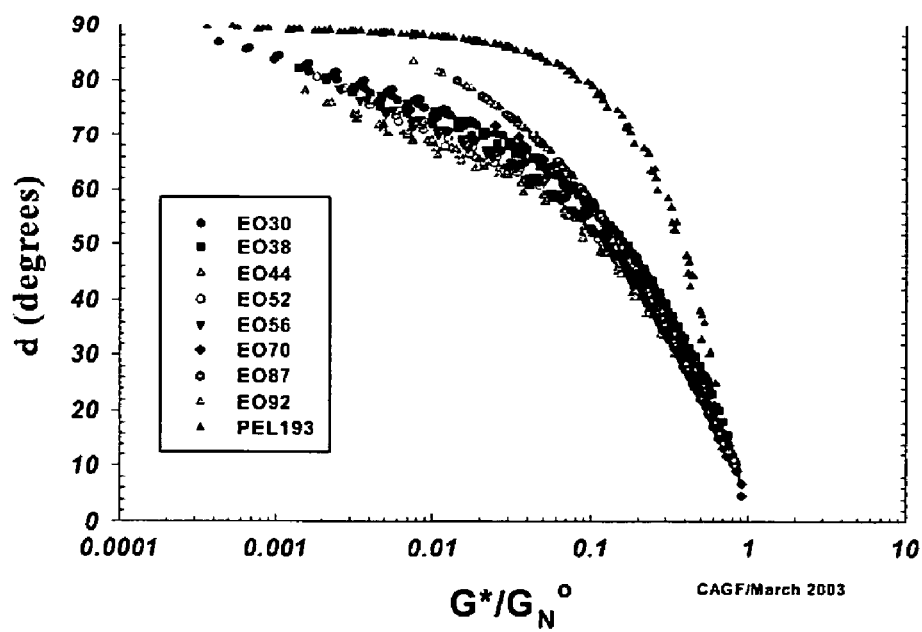
FIG. 10 shows a reduced Van Gurp-Palmen plots.

In another embodiment of the present invention, the behavior of the phase angle, δ may be used as a function of the normalized absolute value of the complex modulus, i. e. |G*|/$G_N^o$ (See Friedrich et al., "Van Gurp-Plamen Plot: a way to characterize polydispersity of linear polymers", Rheol. Acta (2001) 40:322-328; and Friedrich et al., Van Gurp-Palmen Plot II—classification of long chain branched polymers by their topology" Rheol. Acta (2002) 41: 103-113). This can be observed in FIG. 10 where this normalization causes all the curves to collapse, in the region of high |G*|, onto a single one regardless of the content of comonomer. However, in the terminal region, at low values of |G*|/$G_N^o$, the effects of the molecular weight distribution or long chain branching may become evident. Comparative Example 1 is practically monodisperse whereas the ethylene octene copolymer Samples are not. In the terminal region the ethylene/octene copolymers EO87 and EO92, which are the samples richest in octene, as well as the most monodisperse, are between the monodisperse linear Comparative Example 1 and the other copolymers. At this point is difficult to say whether the variations between the ethylene-octene copolymers in the terminal region are due to MWD or the presence of long chain branching.

Figure 11:
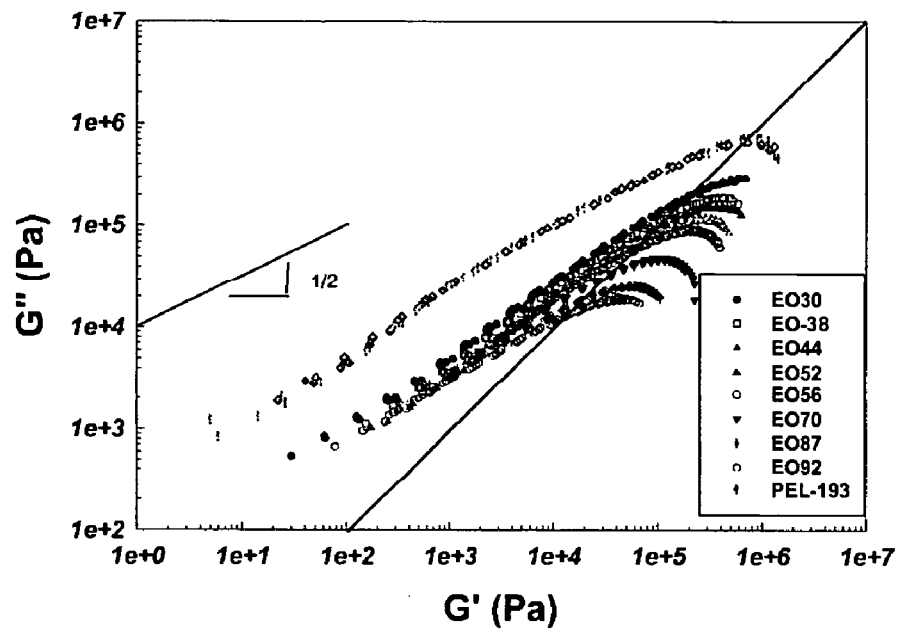
FIG. 11 shows a modified Cole-Cole plots of EO copolymers.

The modified Cole-Cole plots of these ethylene-octene copolymers are shown in FIG. 11, which also includes the linear monodisperse Comparative Example 1. The long solid line is the locus of equal moduli, G'=G"; thus, in the region above this line the behavior is predominantly viscous, whereas in the region beneath this line it is predominantly elastic. The short solid line has a slope of ½. It can be observed that the crossover modulus (i.e., $G_{co}$ (G'=G")) of these ethylene/octene copolymers scales with the octene composition. As the octene content increases, the value of $G_{co}$ decreases. This relationship between $G_{co}$ and the composition is implied by Wu's equation, Eq. (7). Therefore, the crossover modulus $G_{co}$ can also be used to determine the composition of these copolymers. However, if the molecular weight is too high or too low, the crossover modulus might not be observed in the experimental frequency window.

Figure 12:
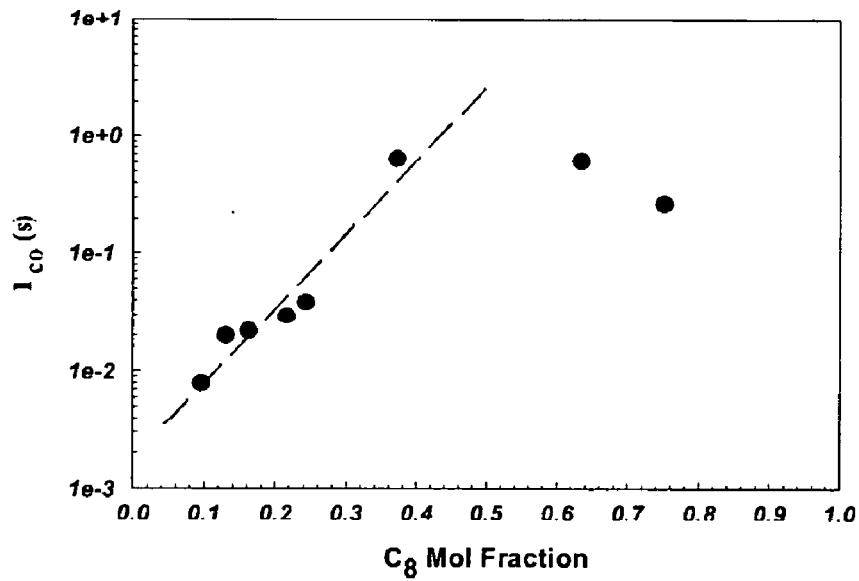
FIG. 12 shows crossover time $\lambda_{co}$ of the EO copolymers vs. copolymer composition.
Figure 13:
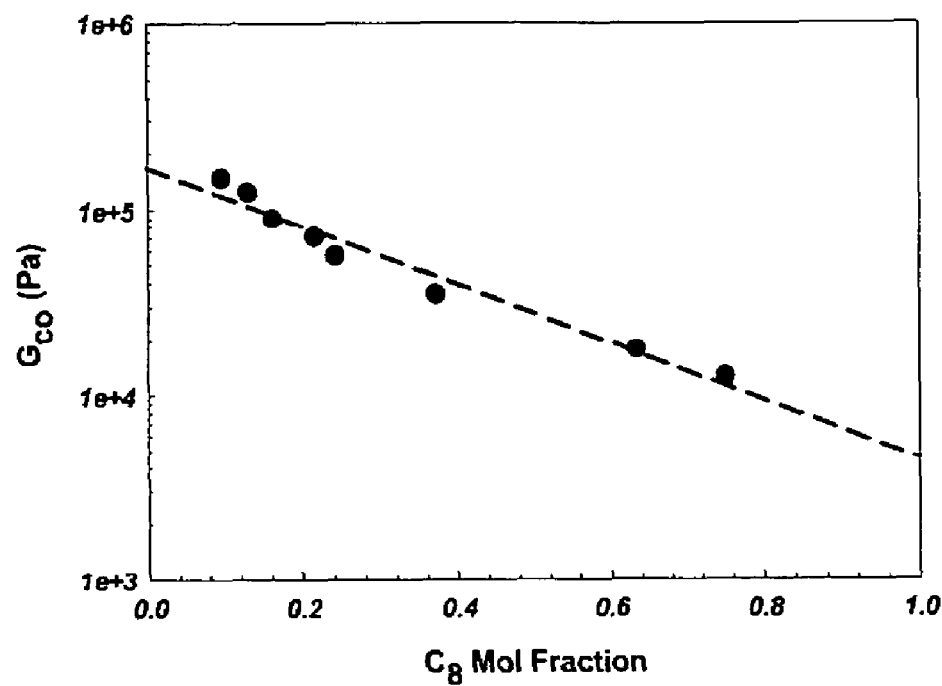
FIG. 13 shows crossover modulus $G_{co}$ vs. copolymer composition.

As stated earlier, the crossover parameters are useful in the rheological characterization of polymer melts. It has been found useful to correlate the effect of the composition of these copolymers on these parameters. The crossover parameters of these ethylene-octene copolymers are given in Table II. FIGS. 12 and 13 show the dependence of $\lambda_{co}$ and $G_{co}$ on the copolymer composition. As shown, it is difficult to separate the effect of the molecular weight and composition up to a mol fraction of 0.372 (copolymer EO70) on the characteristic time. However, it was unexpectedly discovered that the richest octene containing copolymers (EO87 and EO92) break the molecular weight dependence exhibited by the characteristic time of the lower octene content copolymers. Accordingly, crossover parameters may be related to copolymer content via comparison of the crossover parameters of an unknown sample to a calibration curve relating crossover parameters to physical or compositional variable such as, for example, composition or concentration of comonomer present in a copolymer.

As shown in FIG. 13, since $G_{co}$ is dependent on the molecular weight distribution and these copolymers, all of which are relatively narrowly and similarly dispersed, an observed relationship between the crossover modulus and composition, is seen. Accordingly, in an embodiment, the crossover modulus may also be used as a fast rheological means to determine the composition of copolymers, in particular metallocene copolymers.

Figure 14:
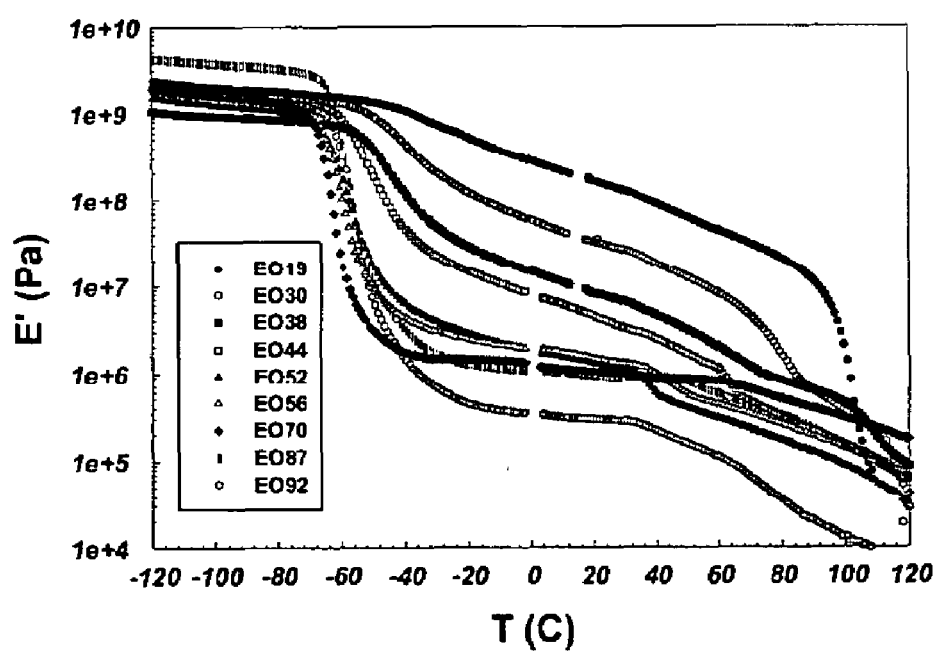
FIG. 14 shows tensile storage modulus vs. temperature.

As earlier established, one of the copolymer characteristics strongly influenced by structure and composition is the thermal dynamic mechanical behavior. The evolution of the storage tensile modulus, E', from the glassy region to the terminal region with increasing temperature for these ethylene-octene copolymers is shown in FIG. 14. It is evident that the magnitude of the modulus and its temperature dependence is strongly influenced by the presence and amount of the octene copolymer. A larger drop of the modulus in the region of the β-relaxation was observed with increasing comonomer content. Also, the onset of the drop of the modulus in the β-relaxation region occurred at lower temperatures with increasing comonomer content. At high temperatures the copolymers with high octene content did not show the same amount of modulus drop that the copolymer with the lowest comonomer content showed.

Figure 15:
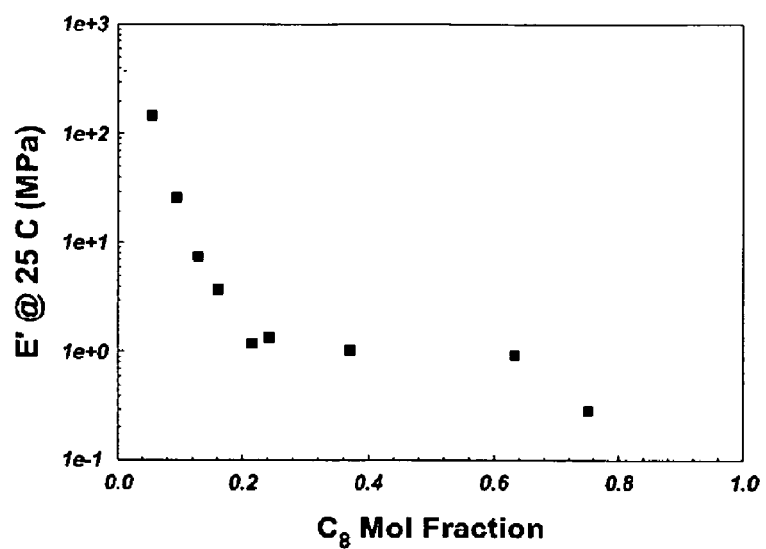
FIG. 15 shows the tensile storage modulus measured at 25° C. vs. copolymer composition.

FIG. 15 shows E' at 25° C. plotted against the copolymer composition. As shown, the tensile modulus decreases with increasing comonomer incorporation which is believed to result from lower crystalline content.

Figure 16:
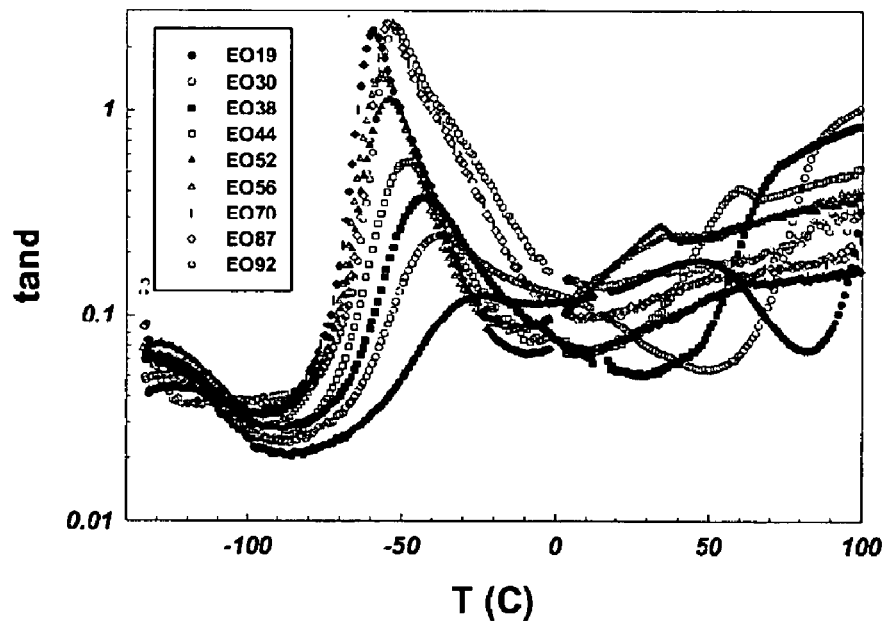
FIG. 16 shows loss tangent vs. temperature.
Figure 17:
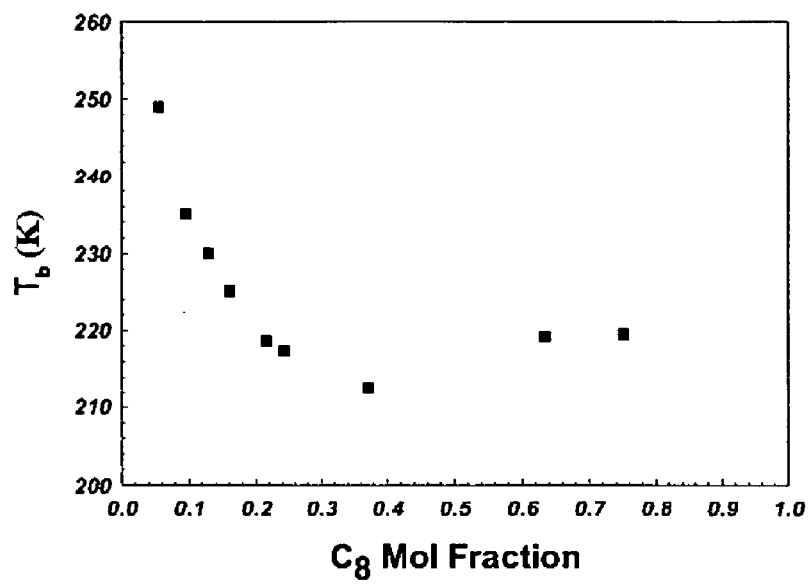
FIG. 17 shows the temperature at the peak of the β-relaxation vs. copolymer composition.
Figure 18:
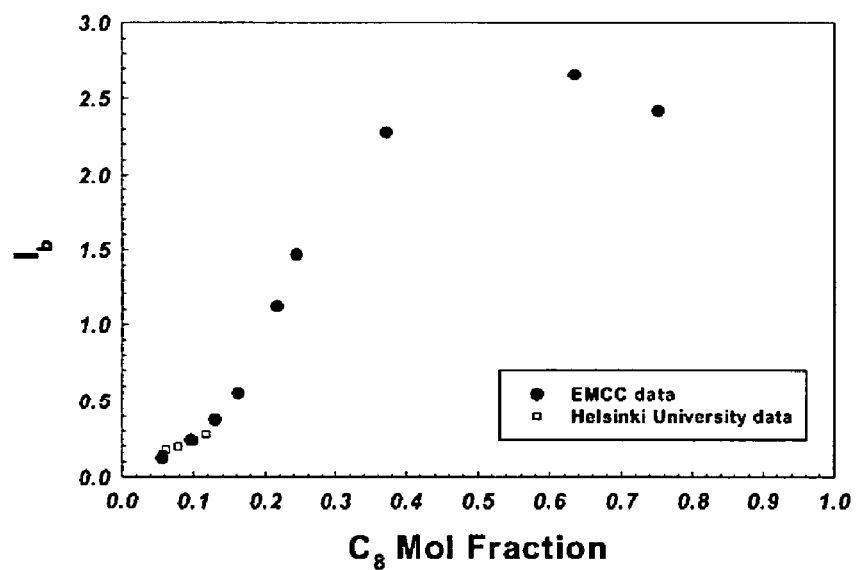
FIG. 18 shows the peak intensity of the β-relaxation vs. copolymer composition.

FIG. 16 shows tan δ against temperature for these ethylene-octene copolymers. The β-relaxation is the most conspicuous relaxation shown by these copolymers. The temperature at its peak, $T_\beta$, the peak intensity $I_\beta$, and the peak breadth are all strongly influenced by the copolymer composition. As shown in FIG. 17, the temperature at the peak of the β-relaxation moved to lower temperatures as the mol fraction of octene increased.

Figure 19:
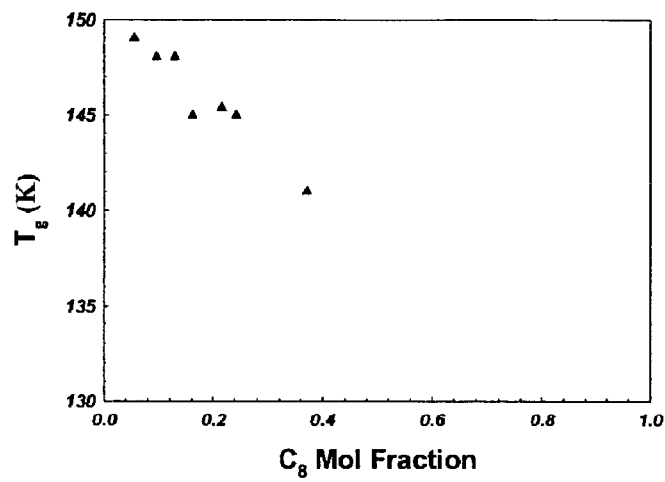
FIG. 19 shows the temperature of the γ-relaxation vs. copolymer composition.

As previously stated, the intensity of the β-transition, $I_\beta$, increased with increasing amount of comonomer. The temperature corresponding to the γ-relaxation is taken as the glass transition temperature, and the data presented in FIG. 14 indicate that the $T_g(=T_\gamma)$ of these copolymers drops as the octene content increases. FIG. 19 shows $T_\gamma$ against the octene mol fraction. The data of some samples at these low temperatures did not allow a clear assignment to $T_\gamma$.

Accordingly, the molecular weight distribution, MWD, may affect the processing and performance of polymers. In an embodiment, the method may include interrelations between MWD and polymer rheology. Such interrelations may be predicated on the assumption that the surrounding network of polymer chains constitutes a time invariant that can be approximated as a fixed tube where the polymer chain reptates. Accordingly, the relaxation modulus, G (t), is proportional to the fraction of all chain segments that have not relaxed after an instantaneous deformation applied at time zero:

$$G(t) = G_N^o \psi(t, \lambda_e) \quad \text{(Eq. 13)}$$

where $\psi(t, \lambda_e)$ is the monodisperse relaxation function and $\lambda_e$ is the reptation time. It is assumed that $\psi(t, \lambda_e)$ is governed by a single time constant since other relaxation times are smaller than the reptation time. Thus, $$\psi(t, \lambda_e) = \exp\left(\frac{-t}{\lambda_e}\right) \quad \text{(Eq. 14)}$$

This single characteristic monodisperse relaxation time, $\lambda_e$, scales with the polymer molecular weight in a power law fashion given by $\lambda_e \propto M^3$. Experimentally, however, it has been observed that the exponent is about 3.4 instead of 3.

In another embodiment, the concept of double reptation may be used to account for polydispersity. This concept may not make a distinction between the reptating chain and the surroundings. It may however be predicated on the dynamics of stress points formed by the entanglements, and thus may assume that at a stress point, two polymer chains are entangled, and the stress will disappears if one chain end reptates through this point. As a consequence, the stress relaxation function, G(t), is given by:

$$\left(\frac{G(t)}{G_N^o}\right)^{\frac{1}{2}} = \int_0^\infty W(M) F^{\frac{1}{2}}(t, M) dM \quad \text{(Eq. 15)}$$

where F(t, M) is the relaxation function for a monodisperse slice of molecular weight M, and W is the weight fraction of chains with molecular weight M.

In another embodiment, the relaxation time may be assumed to depend on both the molecular weight and the molecular weight distribution in terms of an average molecular weight that sets the effect of the environment where the chains of molecular weight $M_i$ reptates. The molecular weight distribution may thus be assumed to be given by a log-normal distribution. This method provides excellent results for commercial grades of polyethylene manufactured with metallocene and Ziegler technologies.

In another embodiment, the following equation may be used to calculate the shear storage and shear loss moduli for copolymers $$G'(\omega) + G''(\omega) = \frac{G_N^o}{\beta \sqrt{\pi}} \int_0^\infty \exp\left[\left(\frac{-1}{\beta} \ln \frac{M}{M_o}\right)^2\right]\left(\frac{A + A^2}{1 + A^2}\right)\frac{dM}{M} \quad \text{(Eq. 16)}$$

where A is given by:

$$A = \omega \frac{\eta_o}{G_N^o} \frac{\left[M_o \exp\left(\frac{-\beta^2}{4}\right)\right]^{1.25}}{\left[M_o \exp\left(\frac{\beta^2}{4}\right)\right]^{3.4}} M^{2.15} \quad \text{(Eq. 17)}$$

The parameters $M_o$ and $\beta$ are defined by the log-normal distribution:

$$M_o = \sqrt{M_w M_n} \quad \text{(Eq. 18)}$$

$$\beta = \sqrt{\ln\left(\frac{M_w}{M_n}\right)^2}$$

Equations 13 and 15 thus show strong dependency of the dynamic moduli on the value of the rubbery plateau modulus $G_N^o$. Accordingly, comparison of the predictions of this formulation for ethylene/octene copolymers using the plateau modulus of polyethylene—assuming no comonomer effect—and the value corrected for comonomer content have been determined.

Figure 20:
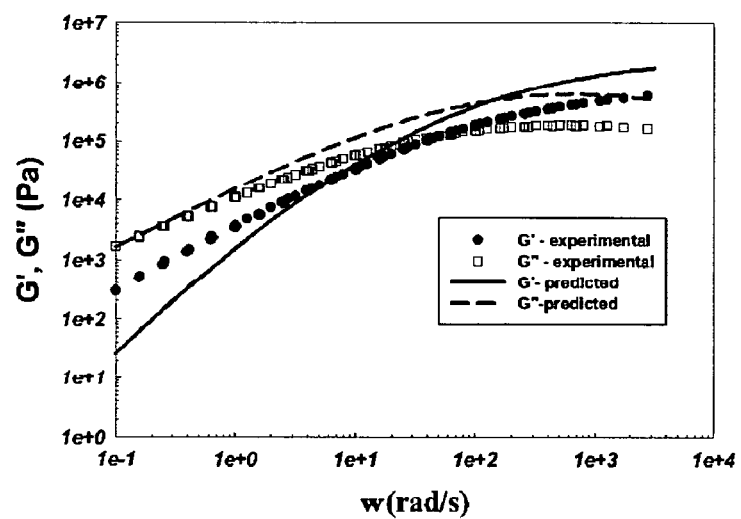
FIG. 20 shows comparison of G' and G" for EO38 with prediction of Eqs. 16-18 using $G_N^o$=2.3 MPa.

As an example, the ethylene-octene copolymer EO38 was analyzed wherein the zero shear viscosity of this polymer was taken as 20 kpa-s. FIG. 20 shows the experimental dynamic moduli of EO38 at 190° C. as well as the dynamic moduli obtained from the MWD using the value of $G_N^o$ for polyethylene, 2.3 MPa. Clearly, a poor agreement of the experimental and predicted data of the dynamic moduli was obtained. As expected, the values of the moduli at high frequencies, and the crossover coordinates are over-predicted.

Figure 21:
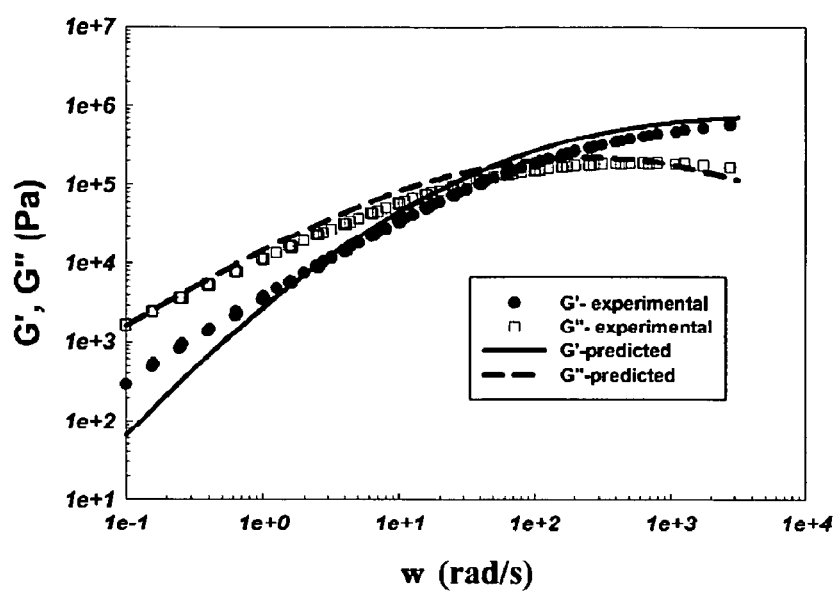
FIG. 21 shows comparison of G' and G" for EO38 with prediction of Eqs. 16-18 using $G_N^o$=0.806 MPa.

However, in another embodiment, a similar comparison of the dynamic moduli predicted using the value of the plateau modulus corrected for comonomer incorporation, 0.806 MPa with the experimental data is presented in FIG. 21. As shown in the figure, the agreement between calculated and experimental values is vastly improved. This simple example shows the strong impact that the plateau modulus has on the rheology of polymer melts, and underlines the importance of the ability to predict the value of $G_N^o$ furnished by the power law models (Equations 4).

The method of the present invention utilizing the calculation of $G_N^o$ based only on the polyolefin chemical structure has been shown validated utilizing otherwise well-defined ethylene-octene copolymers. As such, a scaling relationships between the copolymer composition and various rheological parameters obtainable by robust and relatively fast experimental techniques may be utilized according to the method of the present invention.

Combinatorial Approaches for Science Research

In utilizing the various rheological parameters obtainable by the afore disclosed experimental techniques, a combinatorial approach for identifying or optimizing materials or reactions may be used. Examples include utilization on a large compositional space (e.g., in the context of polymers; of monomers, comonomers, catalysts, catalyst precursors, solvents, initiators, additives, or of relative ratios of two or more of the aforementioned) or a large reaction condition space (e.g., of temperature, pressure and reaction time) may be rapidly explored by preparing libraries and then rapidly screening such libraries. By way of illustration, polymer libraries can comprise, for example, polymerization product mixtures resulting from polymerization reactions that are varied with respect to such factors.

For example, in the context of polymers (but also applicable to other materials), combinatorial approaches for screening a polymer library can include an initial, primary screening, in which polymerization products are rapidly evaluated to provide valuable preliminary data and, optimally, to identify several "hits"—particular candidate materials having characteristics that meet or exceed certain predetermined metrics (e.g., performance characteristics, desirable properties, unexpected and/or unusual properties, etc.). Such metrics may be defined, for example, by the characteristics of a known or standard polymer or polymerization scheme. Because local performance maxima may exist in compositional spaces between those evaluated in the primary screening of the first libraries or alternatively, in process-condition spaces different from those considered in the first screening, it may be advantageous to screen more focused polymer libraries (e.g., libraries focused on a smaller range of compositional gradients, or libraries comprising compounds having incrementally smaller structural variations relative to those of the identified hits) and additionally or alternatively, subject the initial hits to variations in process conditions. Hence, a primary screen can be used reiteratively to explore localized and/or optimized compositional space in greater detail. The preparation and evaluation of more focused polymer libraries can continue as long as the high-throughput primary screen can meaningfully distinguish between neighboring library compositions or compounds.

Once one or more hits have been satisfactorily identified based on the primary screening, polymer and polymerization product libraries focused around the primary-screen hits can be evaluated with a secondary screen—a screen designed to provide (and typically verified, based on known materials, to provide) chemical composition or process conditions that relate with a greater degree of confidence to commercially-important processes and conditions than those applied in the primary screen. In many situations, such improved "real-world-modeling" considerations are incorporated into the secondary screen at the expense of methodology speed (e.g., as measured by sample throughput) compared to a corresponding primary screen. Particular polymer materials, catalysts, reactants, polymerization conditions or post-synthesis processing conditions having characteristics that surpass the predetermined metrics for the secondary screen may then be considered to be "leads." If desired, additional polymer or polymerization product libraries focused about such lead materials can be screened with additional secondary screens or with tertiary screens. Identified lead polymers, monomers, catalysts, catalyst precursors, initiators, additives or reaction conditions may be subsequently developed for commercial applications through traditional bench-scale and/or pilot scale experiments.

While the concept of primary screens and secondary screens as outlined above provides a valuable combinatorial research model for investigating polymers and polymerization reactions, a secondary screen may not be necessary for certain chemical processes where primary screens provide an adequate level of confidence as to scalability and/or where market conditions warrant a direct development approach. Similarly, where optimization of materials having known properties of interest is desired, it may be appropriate to start with a secondary screen. In general, the systems, devices and methods of the present invention may be applied as either a primary, secondary or other screen, depending on the specific research program and goals thereof. See, generally, U.S. Pat. No. 6,653,138 to Turner, et al., for further discussion of a combinatorial approach to polymer science research. Bulk quantities of a particular material may be made after a primary screen, a secondary screen, or both.

According to the present invention, methods, systems and devices are disclosed that improve the efficiency and/or effectiveness of the steps necessary to characterize mechanical and/or physical properties of a material sample or a plurality of samples. In preferred embodiments, in the context of polymer analysis, a property of a plurality of polymer samples or of components thereof can be detected in a polymer characterization system with an average sample-throughput sufficient for an effective combinatorial polymer science research program. Most preferably, the present invention includes determination of comonomer content in a copolymer by relating the comonomer content to the complex modulus of the sample, at a particular phase angle (e.g., a comparison phase angle), and/or determination of comonomer content in a copolymer by relating the comonomer content to the crossover modulus of the sample, at a comparison phase angle.

Figure 1B:
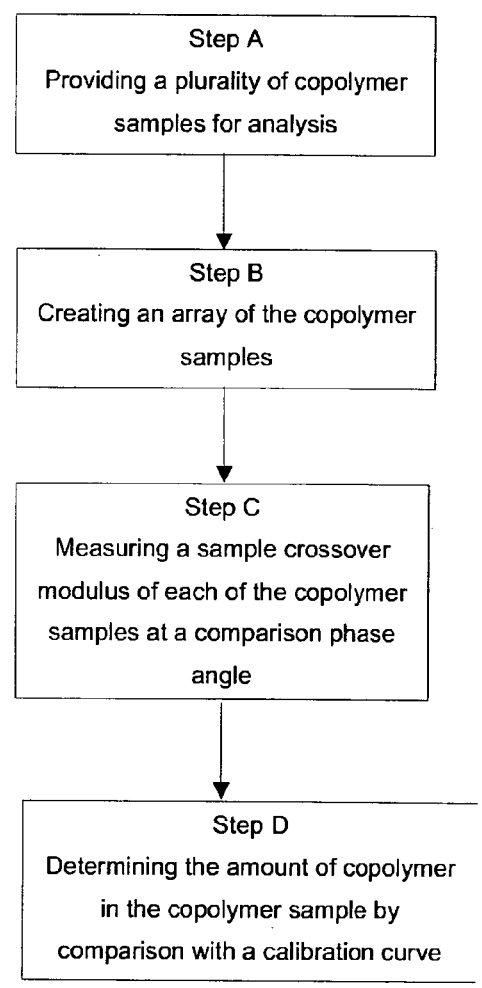
Figure 2:
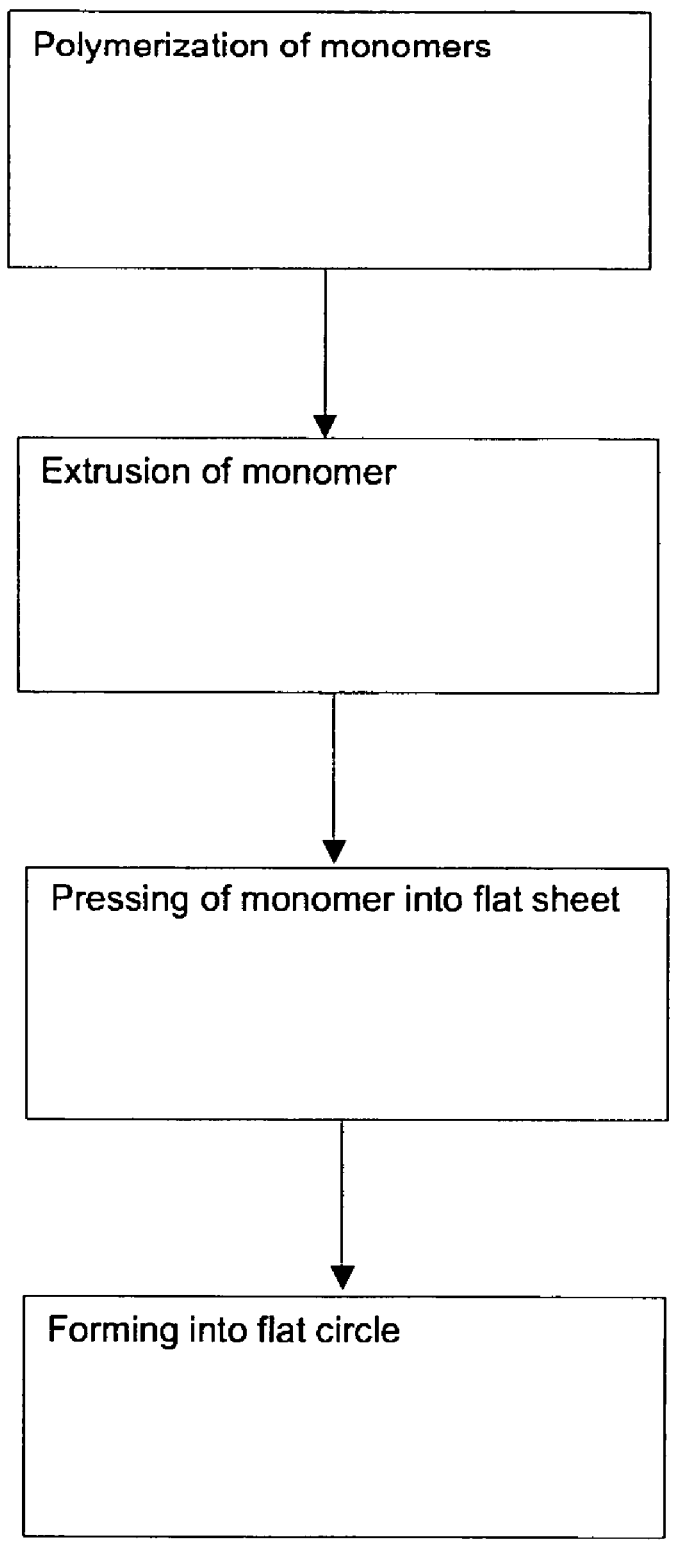
FIG. 2 shows a flowchart of the general steps for sample preparation according to the methods of the present invention.

Referring to FIG. 1, the systems and methods, preferably, start with providing a plurality of samples, e.g., as a library or as an array (e.g., an orderly arrangement) of sample materials that may exhibit one or more predetermined physical/mechanical properties. Ultimately, these predetermined properties will be determined in a determination step, wherein the amount of a component in a copolymer is determined by comparing a measured property (e.g., a complex modulus, a crossover modulus) to a calibration curve which relates that particular measured property to the concentration of the component in the copolymer. However, several prior steps may be effected prior to such a determination.

The sample materials may be prepared for analyst by heating, cooling, blending, extruding, casting, through addition of additives, annealing, and the like. Such preparation is typically designed to affect the properties that are ultimately being determined, and/or to put the sample materials into a form conducive to the measurement to be taken. For example, the sample materials may be melt extruded into a flat sheet of a predetermined thickness, and then cut to a predetermined size and shape required for analysis, e.g., extruding a copolymer sample, followed by pressing the copolymer sample into a flat disk.

In a creating an array of copolymer samples step B, the sample materials may be positioned in a desirable manner for property determination. The materials may be positioned on a substrate, a machine or otherwise positioned to assist in ultimately determining properties of the materials.

It will be appreciated that one of the advantageous features of the present invention is that it affords the ability to screen newly created materials some or all of which are uncharacterized or whose properties are unknown prior to the time of screening. Thus, previously unidentified and uncharacterized new materials can be screened for a common selected property. However, this does not prevent the employment of known references controls or standard as among the library members.

It shall be recognized that sample providing (Step A) and sample array creation (Step B) may be optional steps in property determination protocols, as described above. Also sample preparation and sample array creating may be performed in any order if they are performed. Additionally it should be recognized that sequences other than the order of steps listed above are possible, and the above listing is not intended as limiting.

A measuring of a value of the sample materials (e.g., a stimulation of the sample materials) (Step C) may then be needed to effect one or more responses of the materials. In a preferred embodiment, stimulation of the sample material is in a form consistent with determination of the complex modulus and/or crossover modulus of the material, e.g., rheological stimuli, as described above. Other exemplary stimuli may include force, contact, motion and the like. Exemplary responses include flow, or resistance to flow, deflection, adhesion, deformation, rupture or the like. Negative forces (e.g., compression as opposed to tension, negative pressure as opposed to positive pressure) or the like may also be employed.

In the measuring step, the response or responses of the materials are typically monitored with hardware such as sensors, transducers, load cells or other like devices, preferably directed to determination of rheological properties of the sample material, more preferably directed to determination of the complex modulus of the sample material. Properties of the sample material may then be determined (Step D) quantitatively or qualitatively by relating the responses to the material properties i.e., utilizing first principles, a calibration curve, or the like.

A plurality of samples may be characterized as described above in connection with FIGS. 1a and 1b. As a general approach for improving the sample throughput for a plurality of samples, each of the steps (A) through (D) of FIG. 1 applicable to a given characterization protocol can be optimized with respect to time and quality of information, both individually and in combination with each other. Additionally or alternatively, each or some of such steps can be effected in a rapid-serial, parallel, serial-parallel or hybrid parallel-serial manner.

The throughput of a plurality of samples through a single step in a characterization process may be improved by optimizing the speed of that step, while maintaining—to the extent necessary—the information-quality aspects of that step. Although conventional research norms, developed in the context in which research was rate-limited primarily by the synthesis of samples, may find such an approach less than wholly satisfactory, the degree of rigor can be entirely satisfactory for a primary or a secondary screen of a combinatorial library of samples. For combinatorial research (and as well, for many on-line process control systems), the quality of information is preferably sufficiently rigorous to provide for scientifically acceptable distinctions between the compounds or process conditions being investigated, and for a secondary screen, to provide for scientifically acceptable correlation (e.g., values or, for some cases, trends) with more rigorous, albeit more laborious and time-consuming traditional characterization approaches.

The throughput of a plurality of samples through a series of steps, where such steps are repeated for the plurality of samples, can also be optimized. In one approach, one or more steps of the cycle can be compressed relative to traditional approaches or can have leading or lagging aspects truncated to allow other steps of the same cycle to occur sooner compared to the cycle with traditional approaches. In another approach, the earlier steps of a second cycle can be performed concurrently with the later steps of a first cycle. For example, in a rapid-serial approach for characterizing a sample, sample preparation, delivery to a substrate or the like, for a second sample in a series can be effected before or while the first sample in the series is being screened. As another example, a screen of a second sample in a series can be initiated while the first sample in the series is being screened.

A characterization protocol for a plurality of samples can involve a single-step process (e.g., direct measurement of a property of a sample or of a component thereof) or several steps. In a rapid-serial screen approach for a single-step process, the plurality of samples and a single measuring instrument or other instruments are serially positioned in relation to each other for serial analysis of the samples. In a parallel analysis approach, (e.g., as might be employed by itself, or in an upstream or downstream analysis of the samples relative to a rapid-serial analysis of the present invention) two or more measuring instruments or other apparatus are employed to measure properties (e.g., complex modulus, crossover modulus, and the like) of two or more samples simultaneously.

In a serial-parallel approach, a property of a larger number of samples (e.g., four or more) is screened as follows. First, a property of a subset of the four or more samples (e.g., 2 samples) is screened in parallel for the subset of samples, and then serially thereafter, a property of another subset of four or more samples is screened in parallel. It will be recognized, of course, that plural measuring instruments can be employed simultaneous, or plural measuring instruments can be employed serially.

For characterization protocols involving more than one step, optimization approaches to effect high-throughput characterization can vary. As one example, a plurality of samples can be characterized with a single characterization system (I) in a rapid-serial approach in which each of the plurality of samples ($s_1$, $s_2$, $s_3$ ... $s_n$) are processed serially through the characterization system (I) with each of the steps effected in series on each of the of samples to produce a serial stream of corresponding characterizing property information ($p_1$, $p_2$, $p_3$ ... $p_n$). This approach benefits from minimal capital investment, and may provide sufficient throughput—particularly when the steps have been optimized with respect to speed and quality of information.

As another example, a plurality of samples can be characterized with two or more instruments in a pure parallel (or for larger libraries, serial-parallel) approach in which the plurality of samples ($s_1$, $s_2$, $s_3$ ... $s_n$) or a subset thereof are processed through the two or more measurement systems (I, II, III ... N) in parallel, with each individual system effecting each step on one of the samples to produce the property information ($p_1$, $p_2$, $p_3$ ... $p_n$) in parallel. This approach is advantageous with respect to overall throughput, but may be constrained by the required capital investment.

In a hybrid approach, certain of the steps of the characterization process can be effected in parallel, while certain other steps can be effected in series. Preferably, for example, it may be desirable to effect the longer, throughput-limiting steps in parallel for the plurality of samples, while effecting the faster, less limiting steps in series. Such a parallel-series hybrid approach can be exemplified by parallel sample preparation of a plurality of samples ($s_1$, $s_2$, $s_3$ ... $s_n$), followed by measuring with a single apparatus to produce a serial stream of corresponding characterizing property information ($p_1$, $p_2$, $p_3$ ... $p_n$). In another exemplary parallel-series hybrid approach, a plurality of samples ($s_1$, $s_2$, $s_3$ ... $s_n$) are prepared, measured and correlated in a slightly offset (staggered) parallel manner to produce the characterizing property information ($p_1$, $p_2$, $p_3$ ... $p_n$) in the same staggered-parallel manner.

Optimization of individual characterization steps with respect to speed and quality of information can improve sample throughput regardless of whether the overall characterization scheme involves a rapid-serial or parallel aspect (i.e., true parallel, serial-parallel or hybrid parallel-series approaches). As such, the optimization techniques, while discussed primarily in the context of a rapid-serial approach, are not limited to such an approach, and will have application to schemes involving parallel characterization protocols that may be employed.

Sample Materials

The samples for which the present invention is useful for screening include polymeric materials or any other liquid, semi-solid, or solid material that is capable of being provided as a high viscosity fluid, solid, or other suitable form. Accordingly, without limitation, pure materials, mixtures of materials, bulk materials, particles of materials, thin films of materials, dispersions of materials, emulsions of materials, and solutions of materials are all contemplated as within the useful scope of the present invention.

In a particularly preferred embodiment, the present invention is employed for screening polymer samples, or plastic samples including polymers. Accordingly, unless otherwise stated, reference to screening of polymers or other processing of polymers includes plastics incorporating such polymers. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component can have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

In one embodiment, the polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The systems and methods disclosed herein will have broad application with respect to the type (e.g., architecture, composition, synthesis method or mechanism) and/or nature (e.g., physical state, form, attributes) of the polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. In a preferred embodiment, the sample may comprise a copolymer comprising a $C_2$ to $C_{40}$ monomer, more preferably ethylene, propylene, a butene, a pentene and/or a hexene. The sample may also comprise one or more $C_4$ to $C_{40}$ alpha olefin or diolefin, preferably butene and/or octene. In a preferred embodiment, preferred monomers from which the polymers or copolymers are produced include $C_2$ to $C_{100}$ olefins, more preferably $C_2$ to $C_{60}$ olefins, still more preferably $C_2$ to $C_{40}$ olefins, with preferably $C_2$ to $C_{20}$ olefins still more preferred, and $C_2$ to $C_{12}$ olefins being most preferred. In some embodiments monomers include linear, branched or cyclic alpha-olefins, preferably $C_2$ to $C_{100}$ alpha-olefins, more preferably $C_2$ to $C_{60}$ alpha-olefins, still more preferably $C_2$ to $C_{40}$ alpha-olefins, with $C_2$ to $C_{20}$ alpha-olefins being more preferred, and $C_2$ to $C_{12}$ alpha-olefins most preferred. Examples of preferred olefin monomers include one or more of ethylene, propylene, butene, pentene, hexene, heptene, octene, nonene, decene, dodecene, 4-methyl-pentene-1,3-methyl pentene-1,3,5,5-trimethyl hexene 1, and 5-ethyl-1-nonene.

The polymer or copolymers may include one or more linear or branched $C_3$ to $C_{30}$ prochiral alpha-olefins, or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Preferred monomers may also include aromatic-group-containing monomers containing up to about 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer may further comprise at least one polymerizable double bond such that after polymerization, the aromatic structure will be pendant from the polymer backbone. The aromatic-group containing monomer may further be substituted with one or more hydrocarbyl groups including, but not limited to, $C_1$ to $C_{10}$ alkyl groups. Additionally, two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, paramethyl styrene, 4-phenyl-1-butene, and allyl benzene.

Non-aromatic cyclic group containing monomers are also preferred. These monomers can contain up to about 30 carbon atoms. Suitable non-aromatic cyclic group containing monomers preferably have at least one polymerizable olefinic group that is either pendant on the cyclic structure or is part of the cyclic structure. The cyclic structure may be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinyinorbornene, ethylidene norbornene, cyclopentadiene, cyclopentene, cyclohexene, cyclobutene, vinyladamantane, and the like.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, and triacontadiene. Particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins, with or without substituents at various ring positions.

Non-limiting examples of preferred polar unsaturated monomers include 6-nitro-1-hexene, N-methylallylamine, N-allylcyclopentylamine, N-allyl-hexylamine, methyl vinyl ketone, ethyl vinyl ketone, 5-hexen-2-one, 2-acetyl-5-norbornene, 7-synmethoxymethyl-5-norbornen-2-one, acrolein, 2,2-dimethyl-4-pentenal, undecylenic aldehyde, 2,4-dimethyl-2,6-heptadienal, acrylic acid, vinylacetic acid, 4-pentenoic acid, 2,2-dimethyl-4-pentenoic acid, 6-heptenoic acid, trans-2,4-pentadienoic acid, 2,6-heptadienoic acid, nonafluoro-1-hexene, allyl alcohol, 7-octene-1,2-diol, 2-methyl-3-buten-1-ol, 5-norbornene-2-carbonitrile, 5-norbornene-2-carboxaldehyde, 5-norbornene-2-carboxylic acid, cis-5-norbornene-endo-2,3-dicarboxylic acid, 5-norbornene-2,2,-dimethanol, cis-5-norbornene-endo-2,3-dicarboxylic anhydride, 5-norbornene-2-endo-3-endo-dimethanol, 5-norbornene-2-endo-3-exo-dimethanol, 5-norbornene-2-methanol, 5-norbornene-2-ol, 5-norbornene-2-yl acetate, 1-[2-(5-norbornene-2-yl)ethyl]-3,5,7,9,11,13,15-heptacyclopentylpentacyclo[9.5.1.13,9.15,15.17,13] octasiloxane, 2-benzoyl-5- norbornene, allyl 1,1,2,2,-tetrafluoroethyl ether, acrolein dimethyl acetal, butadiene monoxide, 1,2-epoxy-7-octene, 1,2-epoxy-9-decene, 1,2-epoxy-5-hexene, 2-methyl-2-vinyloxirane, allyl glycidyl ether, 2,5-dihydrofuran, 2-cyclopenten-1-one ethylene ketal, allyl disulfide, ethyl acrylate, and methyl acrylate.

For purposes of this disclosure, the term oligomer refers to compositions having 2-75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

Preferred oligomers for us herein may include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. Other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

As used herein, a copolymer may comprise two, three, four or more different monomer units. Preferred polymers produced herein include homopolymers or copolymers of any of the above monomers. In a preferred embodiment the polymer is a homopolymer of any $C_2$ to $C_{12}$ alpha-olefin. The polymer may be a homopolymer of ethylene or a homopolymer of propylene. In another embodiment the polymer is a copolymer comprising ethylene and one or more of any of the monomers listed above. In still another embodiment, the polymer is a copolymer comprising propylene and one or more of any of the monomers listed above. In a preferred embodiment, the copolymers comprise one or more diolefin comonomers, preferably one or more $C_2$ to $C_{40}$ diolefins.

Preferably, the material may be a copolymer of ethylene and one or more $C_3$ to $C_{20}$ linear, branched or cyclic monomers, preferably one or more $C_3$ to $C_{12}$ linear, branched or cyclic alpha-olefins. Preferably the material is a copolymer of ethylene and one or more of propylene, butene, pentene, hexene, heptene, octene, nonene, decene, dodecene, 4-methyl-pentene-1,3-methyl pentene-1, and 3,5,5-trimethyl hexene 1.

In a preferred embodiment, the polymer is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. The polymer produced herein may also be a copolymer of propylene and one or more of ethylene, butene, pentene, hexene, heptene, octene, nonene, decene, dodecene, 4-methyl-pentene-1,3-methyl pentene-1, and 3,5,5-trimethyl hexene 1.

The copolymers described herein may comprise at least 1 mole % of a first monomer and up to 99 mole % of other monomers. Accordingly, the copolymers described herein may also comprise at least 99 mole % of a first monomer and up to 1 mole % of other monomers. In another embodiment, the polymer comprises: a first monomer present at from 40 to 95 mole %, preferably 50 to 90 mole %, preferably 60 to 80 mole %; a comonomer present at from 5 to 40 mole %, preferably 10 to 60 mole %, more preferably 20 to 40 mole %; and a termonomer present at from 0 to 10 mole %, more preferably from 0.5 to 5 mole %, more preferably 1 to 3 mole %.

In a preferred embodiment, the first monomer comprises one or more of any $C_3$ to $C_8$ linear branched or cyclic alpha-olefins, including propylene, butene, (and all isomers thereof, pentene (and all isomers thereof), hexene (and all isomers thereof), heptene (and all isomers thereof, and octene (and all isomers thereof). Preferred monomers include propylene, 1-butene, 1-hexene, 1-octene, cyclohexene, cyclooctene, hexadiene, cyclohexadiene and the like. The comonomer comprises one or more of any $C_2$ to $C_{40}$ linear, branched or cyclic alpha-olefins (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5- trimethylhexene-1,3-methylpentene-1,4-methylpentene-1, cyclopentadiene, and cyclohexene. The termonomer comprises one or more of any $C_2$ to $C_{40}$ linear, branched or cyclic alpha-olefins, (provided ethylene, if present, is present at 5 mole % or less), including ethylene, propylene, butene, pentene, hexene, heptene, and octene, nonene, decene, un-decene, do-decene, hexadecene, butadiene, hexadiene, heptadiene, pentadiene, octadiene, nonadiene, decadiene, dodecadiene, styrene, 3,5,5-trimethyl hexene-1,3-methyl-pentene-1,4-methylpentene-1, cyclopentadiene, and cyclohexene.

The polymers described above may further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Suitable additives, which may be combined with the copolymer samples, include those employed with olefinic polymers, copolymers and blends. Examples include one or more of the following: heat stabilizers, antioxidants, neutralizers, slip agents, antiblock agents, pigments, antifogging agents, antistatic agents, clarifiers, nucleating agents, ultraviolet absorbers or light stabilizers, fillers, hydrocarbon resins, rosins or rosin esters, waxes, additional plasticizers, hydrogenated hydrocarbon resins, and other plasticizers may be used as modifiers either alone, or in combination with other additives. Effective levels of additives may depend on the details of the copolymer base resin, the fabrication mode, the end application, and the like. Suitable level of additives, when present, are typically less than or equal to about 50 wt %, based on the total weight of the copolymer base resin.

It is within the scope of the present invention to blend additives, other resins and elastomers with the copolymer, which may be polymerized in the presence of the metallocene compound as the catalyst. As such, more than one additive may be added, for example, an antioxidant, an ultraviolet light absorber, an antistatic agent, a flame-retardant, a metal inactivating agent, a pigment, a dye and a nucleating agent, can be added according to the necessity. The preferred amount of additives, which depends on the properties required, is about 20 parts by weight or less, preferably 5 parts by weight or less, based on 100 parts by weight of the copolymer base resin of the present invention.

The copolymer sample of the present invention may also comprise a variety of resins polymerized in the presence of a Ziegler-Natta catalyst, such as a polypropylene resin, high density polyethylene, linear low-density polyethylene, super-low-density polyethylene; polymers produced by the high pressure method such as a low-density polyethylene, poly-olefin resins such as ethylene-vinyl acetate copolymer, ethylene-acrylate copolymer, ethylene-acrylic acid copolymer, ethylene-methacrylic acid copolymer, and ethylene-carbon monoxide copolymer; and a variety of thermoplastic resins including amorphous polystyrene resin, crystalline polystyrene resin, vinyl chloride resin, polyamide resin, polyacetal resin, polycarbonate resin, and the like. When present, the amount of the resin to be blended is preferably about 100 parts by weight or less, more preferably about 50 parts by weight or less, still more preferably about 10 part by weight, per 100 parts by weight of the total copolymer.

The copolymer sample may also comprise elastomers. Preferred elastomers include solid rubbers such as ethylene-propylene rubber, ethylene-1-butene rubber, propylene-1-butene rubber, styrene-butadiene rubber, and/or hydrogenated products thereof. The copolymer may also include elastomers such as polystyrene elastomers, for example styrene-butadiene block copolymeric elastomer can be used. Preferable elastomers also include elastomeric olefin polymers such as ethylene-propylene rubber, ethylene-butene-1 rubber, and propylene-butene-1 rubber, preferably those having a Mooney viscosity of 1 to 100 determined by a method of ASTM D 1646 with the L-rotor at 100° C.

Accordingly, the copolymer sample may be blended with other polymers, particularly with other polyolefins, both in-reactor as well as externally. Specific examples of preferred materials include, but are not limited to, ethylene-propylene rubber, ethylene-propylene diene rubber, and ethylene plastomers such as those commercially available under the trade name EXACT resins (ExxonMobil Chemical Company) AFFINITY and, ENGAGE resins (Dow Chemical Company). Reactor blends with ethylene and/or propylene-based plastomers or elastomers are also within the scope of the invention.

Other copolymers, terpolymers, and the like, which may be used in combination with the copolymer sample include those comprising ethylene and butene in the form of random copolymers and impact copolymers. Random copolymers preferably comprise up to about 6% (by weight) of ethylene or other comonomers inserted at random within the backbone chain of the polymer thereby reducing the crystallinity and the melting point by introducing irregularities into the chain. Random copolymers may be used to improve optical clarity, to lower melting point, or when a lower modulus is desirable. See for example U.S. Pat. No. 6,583,227.

Impact copolymers, also known as heterophasic copolymers, preferably comprise up to about 40 wt % ethylene-propylene rubber (EPR), intimately dispersed within the matrix, usually a homopolymer. An EPR comprising about 50 wt % ethylene, translates into about 8% to about 20% ethylene level on the total material, depending on the rubber amount incorporated. As implied in the name, impact copolymers preferably improve impact strength of the article, especially at low temperatures. (see 'Polypropylene Handbook' (edited by Edward P. Moore) page 5, Hanser Publishers, 1996.

Examples of impact copolymers suitable for use herein include those described in U.S. Pat. No. 5,258,464 directed to propylene impact copolymers with improved resistance to "stress whitening"; In U.S. Pat. No. 5,362,782, a nucleating agent is added to propylene impact copolymers having a numerical ratio of the intrinsic viscosity of the copolymer rubber phase (second component) to the intrinsic viscosity of the homopolymer phase (first component) which is near unity, and an ethylene content of the copolymer phase in the range of 38% to 60% by weight. These propylene impact copolymers are described as producing articles having good clarity as well as impact strength and resistance to stress whitening. The nucleating agents increase stiffness and impact strength; U.S. Pat. No. 5,250,631 directed to a propylene impact copolymer having a homopolypropylene first component and an ethylene/butene/propylene terpolymer second component to obtain high impact strength coupled with resistance to stress whitening; U.S. Pat. No. 5,948,839, directed to an impact copolymer containing a first component and 25 to 45 weight percent ethylene/propylene second component having from 55 to 65 weight percent ethylene, to produce a composition having a melt flow of from 7 to 60 dg/min; and U.S. Pat. No. 5,990,242, directed to using an ethylene/butene (or higher alpha-olefin) copolymer second component, rather than a propylene copolymer, prepared using a hafnocene type metallocene. See also U.S. Pat. Nos. 6,492,266, 6,492,473, 6,492,465, 6,472,474, 6,399,707, 6,384,142, 6,342,566, 6,288,171, 6,268,438, 6,225,412, 6,111,039, 6,087,459, 5,747,592, 5,225,483, 5,066,723, 5,011,891, and 4,843,129, all of which are fully incorporated by reference herein.

In an embodiment, a polymer or copolymer sample may be a heterogeneous sample comprising one or more polymer components, one or more monomer components and/or and an additional phase which may be a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, fillers, reinforcements, flame retardants, colorants, environmental protectants, other performance modifiers, control agents, plasticizers, cosolvents and/or accelerators, among others. In this regard, the present invention is particularly attractive for the screening of effects of variations of additives upon the characteristics of the material. The various components of the heterogeneous polymer sample can be uniformly or non-uniformly dispersed in the continuous fluid phase.

In one preferred embodiment, the polymer samples of the present invention are melted or otherwise heated to a high viscosity fluid state, with the resulting material constituting a high viscosity fluid sample. Heating may be performed simultaneously while the samples are on a common substrate. Alternatively, the sample is heated to liquefy it or maintain its liquidity while being transferred to a common substrate (e.g., while in a probe of an automated sampler).

In another embodiment at a point prior to, during, or after depositing the sample onto the substrate, the polymer sample is preferably, chemically treated to form a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a form that includes well-dissolved chains and/or dissolved aggregated micelles. The solvent can vary, depending on the application, for example with respect to polarity, volatility, stability, and/or inertness or reactivity. Typical solvents include, for example, tetrahydrofuran (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being an emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 1 nm to about 500 nm, more typically from about 5 nm to about 300 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 µm (micrometers) to about 1000 µm, more typically from about 0.4 µm to about 500 µm, and even more typically from about 0.5 µm to about 200 µm.

Exemplary polymers that can be in the form of neat polymer samples include dendrimers, and siloxane, among others. The high viscosity fluid polymer sample can also be employed in the form of a slurry, a latex, a microgel, a physical gel, or in any other form sufficient for creating an array for screening analysis as described and claimed herein. In some cases, polymer synthesis reactions (i.e., polymerizations) directly produce high viscosity fluid samples. In other cases, the polymer may be synthesized, stored or otherwise available for characterization in a non-liquid physical state, such as a solid state (e.g., crystalline, semicrystalline or amorphous), a glassy state or rubbery state. The polymer sample can, regardless of its particular form, have various attributes, including variations with respect to polarity, solubility and/or miscibility.

In preferred applications, the polymer sample is a polymerization product mixture. As used herein, the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate vessels at various times during the course of the synthesis, optionally with addition of more solvent or other reagents to arrest the synthesis reaction or prepare the samples for analysis. These intermediate samples can then be characterized at any time without interrupting the synthesis reaction.

It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated.

The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be free radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

It will be appreciated that in certain embodiments, a polymer sample is formed in situ on a substrate, post synthesis treated in situ on a substrate, or a combination thereof. Examples of such post synthesis treatment steps include for instance, heat treating, environmental exposure (e.g., temperature moisture, radiation, chemicals, etc.), aged, or the like.

In other preferred embodiments, polymer or other sample materials may be provided as solids or semi-solids. Such samples may be provided in a variety of geometric configurations such as blocks, cylinders, loops, films and the like. Generally, geometric configurations are selected to be appropriate for one or more tests that are to be performed upon the samples. Solid and semi-solid samples may be rigid, elastic, gelatinous or otherwise. In one preferred embodiment, samples are provided in a tacky state, and thus exhibits at least some degree of adhesiveness within the range of temperature under examination. Samples may also be specifically arranged for testing. For example, samples may be interwoven as a fabric, unwoven, machined to shape, molded to shape, cut to shape or otherwise physically manipulated for testing.

Sample Size

The sample size may not be narrowly critical, and can generally vary, depending on the particular characterization protocols and systems used to analyze the sample or components thereof. However, it will be appreciated that the present invention advantageously permits for attaining reliable data with relatively small samples. Typical sample sizes can range from about 0.1 microgram to about 1 gram, more typically from about 1 microgram to about 100 milligrams, even more is typically from about 5 micrograms to about 1000 micrograms, and still more typically from about 20 micrograms to about 50 micrograms.

If and when placed on a substrate for forming a library, as discussed herein with regard to sampling, the samples may be dispensed with any suitable dispensing apparatus (e.g., an automated micropipette or capillary dispenser, optionally with a heated tip). Each sample of the library is dispensed to an individually addressable region on the substrate. Generally, each sample occupies no more than about 1000 square milli meters ($mm^2$) of area on a substrate surface, preferably no more than about 100 $mm^2$, more preferably no more than about 50 $mm^2$, even more preferably no more than about 10 $mm^2$, most preferably no more than about 5 $mm^2$, and it is possible for a sample to occupy less than about 1 $mm^2$. The sample is preferably to have a thickness that is less than about 500 microns, preferably less than about 100 microns, even more preferably less than about 10 microns, most preferably less than about 5 microns, and it is possible for a sample to have a thickness that is less than about 1 microns.

In applications where the sample is disposed in a well, preferably the sample size does not exceed about 1000 milligrams. Accordingly, for dispensing high viscosity fluid samples, the individual samples are each dispensed in amounts no greater than about 100 ml, more preferably no greater than about 10 ml and still more preferably no greater than about 1 ml.

Libraries of Sample Materials

Libraries of samples may have 2 or more samples that are physically or temporally separated from each other—for example, by residing in different regions of a common substrate, in different substrates, in different sample containers of a common substrate, by having a membrane or other partitioning material positioned between samples, or otherwise. The plurality of samples preferably has at least 4 samples and more at least 8 samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Four samples are also a minimum number of samples to effect a serial-parallel characterization approach, as described above (e.g., with two analytical instruments operating in parallel). Eight samples can provide for additional variations in the explored factor space (e.g., eight samples corresponds to the number of parallel polymerization reactors in the PPR-8.TM., being selectively offered as one of the Discovery Tools.TM. of Symyx Technologies, Inc. (Santa Clara, Calif.)), which can be used to prepare polymers for screening in accordance with the present invention. Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of other parallel reactor configurations for synthesizing materials for screening herein (e.g., the PPR-48.TM., Symyx Technologies, Inc.) or of standard sample containers (e.g., 96-well microtiter plate-type formats). Moreover, even larger numbers of samples can be characterized according to the methods of the present invention for larger scale research endeavors. Hence, for screening of polymers or other materials the number of samples can be 150 or more, 400 or more, 500 or more, 750 or more, 1,000 or more, 1,500 or more, 2,000 or more, 5,000 or more and 10,000 or more samples. As such, the number of samples can range from about 2 samples to about 10,000 samples or more, and preferably from about 8 samples to about 10,000 or more samples. In many applications, however, the number of samples can range from about 80 samples to about 1500 samples.

In some cases, in which processing of samples using typical 96-well microtiter-plate formatting or scaling is convenient or otherwise desirable, the number of samples can be 96*N, where N is an integer ranging from about 1 to about 100 or greater. For many applications, N can suitably range from 1 to about 20, and in some cases, from 1 to about 5.

A library of samples comprises two or more different samples spatially separated—preferably, but not necessarily on a common substrate, or temporally separated. Candidate samples (i.e., members) within a library may differ in a definable and typically predefined way, including with regard to chemical structure, processing (e.g., synthesis) history, mixtures of interacting components, post-synthesis treatment, purity, etc. The samples are spatially separated, preferably at an exposed surface of the substrate, such that the library of samples is separately addressable for characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. The use of reference standards, controls or calibration standards may also be performed, though it is not necessary. Further, a library may be defined to include subgroups of members of different libraries, or it may include combinations of plural libraries. The samples of a library may be previously characterized, uncharacterized or a combination thereof, so that property information about the samples may not be known before screening.

Typically, for combinatorial science research applications, at least two or more, preferably at least four or more, even more preferably eight or more and, in many cases, most preferably each of the plurality of polymer samples in a given library of samples will be different from each other. Specifically, a different sample can be included within at least about 50%, preferably at least 75%, preferably at least 80%, even more preferably at least 90%, still more preferably at least 95%, yet more preferably at least 98% and most preferably at least 99% of the samples included in the sample library. In some cases, all of the samples in a library of samples will be different from each other.

In one embodiment, preferably at least eight samples are provided in a library on a substrate and at least about 50% of the samples included in the library are different from each other. More preferably, the library includes at least 16 samples and at least 75% of said samples included in said library are different from each other. Still more preferably, the library includes at least 48 samples and at least 90% of said samples included in the library are different from each other.

The substrate can be a structure having a rigid or semi-rigid surface on which or into which the library of samples can be formed, mounted, deposited or otherwise positioned. The substrate can be of any suitable material, and preferably includes materials that are inert with respect to the samples of interest, or otherwise will not materially affect the mechanical or physical characteristics of one sample in an array relative to another. Exemplary polymeric materials that can be suitable as a substrate material in particular applications include polyimides such as Kapton.TM., polypropylene, polytetrafluoroethylene (PTFE) and/or polyether etherketone (PEEK), among others. The substrate material is also preferably selected for suitability in connection with known fabrication techniques. Metal or ceramic (e.g., stainless steel, silicon, including polycrystalline silicon, single-crystal silicon, sputtered silicon, and silica ($SiO_2$) in any of its forms (quartz, glass, etc.)) are also preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Another suitable substrate is a silicon wafer that has been patterned to define a predetermined configuration on which the sample or samples are deposited (e.g., suspended deflectable arms). As to form, the sample containers formed in, at or on a substrate can be preferably, but are not necessarily, arranged in a substantially flat, substantially planar surface of the substrate. The sample containers can be formed in a surface of the substrate as dimples, spots, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications.

In certain preferred embodiments, the substrate is formed to securely maintain contact with a plurality of samples. According to various methodologies it may be desirable to place forces on samples while the samples remain secured to the substrate. Forces may be applied to the samples by one or more members separate from the substrate or the substrate may apply the forces.

In one particularly preferred embodiment, the library includes a combinatorial library of polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time), post-synthesis treatment, or any other factor affecting polymerization or material properties. Design variables for polymerization reactions are well known in the art. See generally, Odian, Principles of Polymerization, 3rd Ed., John Wiley & Sons, Inc. (1991). A library of polymer samples may be prepared in parallel polymerization reactors or in a serial fashion. Exemplary methods and apparatus for preparing polymer libraries—based on combinatorial polymer synthesis approaches—are disclosed in U.S. Pat. No. 6,489,168 to Wang, U.S. Pat. No. 6,455,316 to Turner et al.

Sample Handling

Handling of sample materials may be accomplished with a plurality of steps which include withdrawing a sample from a sample container and delivering at least a portion of the withdrawn sample to a substrate. Handling may also include additional steps, particularly and preferably, sample preparation steps. In one approach, only one sample is withdrawn into a suitable liquid or solid dispensing device and only one sample resides in the probe at one time. In other embodiments, multiple samples may be drawn. In still other embodiments, multiple dispensers may be used in parallel.

When creating an array of copolymer samples, the samples may be prepared, at least in part, by extruding a copolymer sample in a molten state, followed by pressing and forming the copolymer sample into a flat disk. Also, the array of samples may be created by combining a copolymer sample with a solvent to produce a solution, a suspension, an emulsion, or the like, followed by depositing at least a portion of the combined copolymer sample and the solvent on a surface. Next, removing at least a portion of the solvent, preferably all of the solvent, followed by pressing and forming the copolymer sample into a flat disk or other form consistent with analysis.

In the general case, handling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system in a fully automated manner—for example, with an autosampler.

In one embodiment, handling may be done using a microprocessor controlling an automated system (e.g., a robot arm). Preferably, the microprocessor is user-programmable to accommodate libraries of samples having varying arrangements of samples (e.g., square arrays with "n-rows" by "n-columns", rectangular arrays with "n-rows" by "m-columns", round arrays, triangular arrays with "r-" by "r-" by "r-" equilateral sides, triangular arrays with "r-base" by "s-" by "s-" isosceles sides, etc., where n, m, r, and s are integers).

Overview of Instruments and Methods

The present invention comprises instruments and methods for screening the mechanical or physical properties of a combinatorial library of materials by using at least one response sensing device to measure the responses of individual library members to forces applied by at least one force application source.

In a preferred embodiment, the system may be driven by suitable software for designing the library, controlling the instruments for mechanical property screening, and data acquisition, viewing and searching, such as LIBRARY STUDIO.TM., by Symyx Technologies, Inc. (Santa Clara, Calif.); IMPRESSIONIST.TM., by Symyx Technologies, Inc. (Santa Clara, Calif.); EPOCH.TM., by Symyx Technologies, Inc. (Santa Clara, Calif.); or a combination thereof. Additionally, the system may also use a database system to store and retrieve data with the overlays. The software preferably provides graphical user interfaces to permit users to design libraries of materials by permitting the input of data concerning the precise location on a substrate of a material (i.e., the address of the material). Upon entry, the software will execute commands to control movement of the robot, for controlling activity at such individual address. The versatile instruments and methods of the present invention can screen libraries of materials based on many different mechanical properties relating to Young's modulus (e.g., flexure, uniaxial extension, biaxial compression, and shear), failure (stress and strain at failure, toughness), adhesion, and others.

The instruments and methods of the present invention can conduct parallel, rapid-serial, serial-parallel and hybrid parallel-serial mechanical properties characterization. Some instruments and methods embodiments of the present invention are directed to parallel characterization of material samples, while others are directed to rapid serial or serial-parallel characterization of material samples. Throughout this specification, the specific preferred embodiments discussed in detail below are parallel embodiments. These particularly preferred embodiments have many detailed features, which may not be necessary in other embodiments of this invention. For example, less number of response sensing devices may be required in the rapid serial embodiments compared to the preferred parallel embodiments. Another example is that response sensing devices are placed remotely to the samples and are set at certain spacing in the preferred parallel embodiments. Those of skill in the art can easily modify such design parameters for other embodiments, such as by placing the response sensing devices at other spacing, not placing the response sensing devices substantially in a plane, etc. These are design choices for the present invention and describe other embodiments of the invention.

The several aspects of the characterization methods and systems disclosed and claimed herein can be advantageously employed separately, or in combination to efficiently characterize a variety of materials, with particular emphasis on polymeric materials. In an embodiment, preferred materials include alpha olefin copolymers with still more preferred materials including ethylene copolymers. In preferred embodiments, these features are employed in combination to form a polymer characterization system that can operate as a high-throughput screen in a materials science research program directed to identifying and optimizing new materials, for instance, new polymers, new catalysts, new polymerization reaction conditions and/or new post-synthesis processing conditions. Certain characterizing information—particularly information obtainable from the present invention are broadly useful for characterizing polymers and polymerization reactions. As such, the particular materials and/or mechanisms disclosed herein should be considered exemplary of the invention and non-limiting as to the scope of the invention, which may be applicable in a variety of applications.

Environmental Control Device

Since the mechanical properties of materials can depend strongly on environmental conditions—temperature, pressure, ambient gas composition (including humidity), electric and magnetic field strength, and so on—the screening instruments discussed above may include a control system for regulating environmental conditions. Useful control systems include an environmental chamber that encloses the sample, the sample holder, and the like. The system may also uses computer software to regulate conditions in the environmental chamber. As discussed below, the system may locate the response sensing device outside of the environmental chamber if their performance is strongly influenced by any of the environmental control variables, such as temperature. Measurements may be performed as a function of the value of one or more of these quantities, or may be performed as a function of time elapsed after a change in the value of one or more of these quantities.

For methods directed to characterizing a plurality of samples, a property of each of the samples or of one or more components thereof is detected—serially or in a parallel, serial-parallel or hybrid parallel-serial manner—at an average sample throughput of not more than about 10 minutes per sample. As used in connection herewith, the term "average sample throughput" refers to the sample-number normalized total (cumulative) period of time required to detect a property of two or more samples with a characterization system. The total, cumulative time period is delineated from the initiation of the characterization process for the first sample, to the detection of a property of the last sample or of a component thereof, and includes any intervening between-sample pauses in the process. The sample throughput is more preferably not more than about 8 minutes per sample, even more preferably not more than about 4 minutes per sample and still more preferably not more than about 2 minutes per sample. Depending on the quality resolution of the characterizing information required, the average sample throughput can be not more than about 1 minute per sample, and if desired, not more than about 30 seconds per sample, not more than about 20 seconds per sample or not more than about 10 seconds per sample, and in some applications, not more than about 5 seconds per sample and not more than about 1 second per sample. Sample-throughput values of less than 4 minutes, less than 2 minutes, less than 1 minute, less than 30 seconds, less than 20 seconds and less than 10 seconds are demonstrated in the examples. The average sample-throughput preferably ranges from about 10 minutes per sample to about 10 seconds per sample, more preferably from about 8 minutes per sample to about 10 seconds per sample, even more preferably from about 4 minutes per sample to about 10 seconds per sample and, in some applications, most preferably from about 2 minutes per sample to about 10 seconds per sample.

As for screening throughput for parallel embodiments, up to 96 library members may have their mechanical properties measured simultaneously in about 10 minutes or less, preferably about 5 minutes or less and even more preferably in about 1 minute or less. In some parallel embodiments, screening throughput of even about 30 seconds or less may be accomplished for an array of the sizes discussed herein, e.g., up to 96 samples or members in the array.

A sample-throughput of 10 minutes per sample or less is important for a number of reasons. Systems that detect a property of a sample or of a component thereof at the aforementioned sample throughput rates can be employed effectively in a combinatorial research program. From a completely practical point of view, the characterization rates are also roughly commensurate with reasonably-scaled polymer sample library synthesis rates. It is generally desirable that combinatorial screening systems, such as the polymer characterization protocols disclosed herein, operate with roughly the same sample throughput as combinatorial synthesis protocols—to prevent a backlog of uncharacterized polymerization product samples. Hence, because moderate scale polymer-synthesis systems, such as the Discovery Tools.TM. PPR-48.TM. (Symyx Technologies, Santa Clara Calif.), can readily prepare polymer libraries with a sample-throughput of about 100 polymer samples per day, a screening throughput of about 10 minutes per sample or faster is desirable. Higher throughput synthesis systems demand higher characterization throughputs. The preferred higher throughput values are also important with respect to process control applications, to provide near-real time control data.

Additionally, as shown in connection with the examples provided herein, the characterization of polymer samples at such throughputs can offer sufficiently rigorous quality of data, to be useful for scientifically meaningful exploration of the material compositional and/or reaction conditions research space.

Other Screens

The present invention may be employed by itself or in combination with other screening protocols for the analysis of polyolefins. Without limitation, examples of such screening techniques include those addressed in U.S. Pat. Nos. 6,182,499 (McFarland, et al); 6,175,409 B1 (Nielsen, et al); 6,157,449 (Hajduk, et al); 6,151,123 (Nielsen); 6,034,775 (McFarland, et al); 5,959,297 (Weinberg, et al), and 5,776,359 (Schultz, et al.

Screening techniques may also include (without limitation) optical screening, infrared screening, electrochemical screening, flow characterization (e.g., gas, liquid or gel-phase chromatography), spectrometry, crystallography, or the like.

It will be appreciated from the above that many alternative embodiments exist for high throughput mechanical property screening within the scope of the present invention. Accordingly, the instruments and methods discussed above are to be considered exemplary and nonlimiting as to the scope of the invention.

Accordingly, the present invention includes:

1a. A high throughput method to determine an amount of a comonomer in a copolymer sample, the method comprising the steps of:
   a) providing a plurality of copolymer samples;
   b) creating an array of the copolymer samples;
   c) measuring a sample complex modulus of each of the copolymer samples at a comparison phase angle;
   d) determining the amount of a comonomer in the copolymer sample by comparing the sample complex modulus to a calibration curve, wherein the calibration curve relates a concentration of the comonomer in the copolymer sample to a complex moduli of the copolymer sample determined at the comparison phase angle.

2a. The method of 1a, wherein the step of providing a plurality of copolymer samples comprises providing a plurality of copolymers comprising ethylene, propylene, or both ethylene and propylene.

3a. The method according to any of 1a or 2a, wherein the copolymer samples comprise a $C_4$ to $C_{40}$ alpha olefin.

4a. The method according to any of 1a to 3a, wherein the comparison phase angle is about 5 to about 85°.

5a. The method according to any of 1a to 4a, wherein the comparison phase angle is about 20 to about 60°.

6a. The method according to any of 1a to 5a, wherein the comparison phase angle is about 30 to about 40°.

7a. The method according to any of 1a to 6a, wherein two or more of the sample complex moduli are measured simultaneously.

8a. The method according to any of 1a to 7a, wherein the creating an array of the copolymer samples step includes extruding a copolymer sample in a molten state, followed by pressing and forming the copolymer sample into a flat disk.

9a. The method according to any of 1a to 8a, wherein the creating an array of the copolymer samples step includes combining a copolymer sample with a solvent, depositing at least a portion of the combined copolymer sample and the solvent on a surface, removing at least a portion of the solvent, followed by pressing and forming the copolymer sample into a flat disk.

10a. A high throughput method to determine an amount of a comonomer in a copolymer sample, the method comprising the steps of:
   a) providing a plurality of copolymer samples;
   b) creating an array of the copolymer samples;
   c) measuring a sample crossover modulus of each of the copolymer samples at a comparison phase angle;
   d) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

11a. The method according to 10a, wherein the step of providing a plurality of copolymer samples comprises providing a plurality of copolymers comprising ethylene, propylene, or both ethylene and propylene.

12a. The method according to any of 10a or 11a, wherein the copolymer samples comprise a $C_4$ to $C_{40}$ alpha olefin.

13a. The method according to any of 10a to 12a, wherein the comparison phase angle is about 5 to about 85°.

14a. The method according to any of 10a to 13a, wherein the comparison phase angle is about 20 to about 60°.

15a. The method according to any of 10a to 14a, wherein the comparison phase angle is about 30 to about 40°.

16a. The method according to any of 10a to 15a, wherein two or more of the sample crossover moduli are measured simultaneously.

17a. The method according to any of 10a to 16a, wherein the creating an array of the copolymer samples step includes extruding a copolymer sample in a molten state, followed by pressing and forming the copolymer sample into a flat disk.

18a. The method according to any of 10a to 17a, wherein the creating an array of the copolymer samples step includes combining a copolymer sample with a solvent, depositing at least a portion of the combined copolymer sample and the solvent on a surface, removing at least a portion of the solvent, followed by pressing and forming the copolymer sample into a flat disk.

19a A method to determine an amount of a comonomer in a copolymer sample, the method comprising the steps of:
   a) providing a copolymer sample;
   b) measuring a sample crossover modulus of the copolymer sample at a comparison phase angle;
   c) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

20a. The method according to 19a, wherein the copolymer sample comprises ethylene, propylene, or both ethylene and propylene.

21a. The method according to any of 19a or 20a, wherein the copolymer sample comprise a $C_4$ to $C_{40}$ alpha olefin.

22a. The method according to any of 19a to 21a, wherein the comparison phase angle is about 5 to about 85°.

23a. The method according to any of 19a to 22a, wherein the comparison phase angle is about 20 to about 60°.

24a. The method according to any of 19a to 23a, wherein the comparison phase angle is about 30 to about 40°.

25a. The method according to any of 19a to 24a, wherein the providing a copolymer sample step includes extruding the copolymer sample in a molten state, followed by pressing and forming the copolymer sample into a flat disk.

26a. The method according to any of 19a to 25a, wherein the providing a copolymer sample step includes combining a copolymer sample with a solvent, depositing at least a portion of the combined copolymer sample and the solvent on a surface, removing at least a portion of the solvent, followed by pressing and forming the copolymer sample into a flat disk.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

We claim:

1. A high throughput method to determine an amount of a comonomer in a copolymer sample, the method comprising the steps of:
   a) providing a plurality of copolymer samples;
   b) creating an array of the copolymer samples;
   c) measuring a sample complex modulus of each of the copolymer samples at a comparison phase angle;
   d) determining the amount of a comonomer in the copolymer sample by comparing the sample complex modulus to a calibration curve, wherein the calibration curve relates a concentration of the comonomer in the copolymer sample to a complex moduli of the copolymer sample determined at the comparison phase angle.

2. The method of claim 1, wherein the step of providing a plurality of copolymer samples comprises providing a plurality of copolymers comprising ethylene, propylene, or both ethylene and propylene.

3. The method of claim 1, wherein the copolymer samples comprise a $C_4$ to $C_{40}$ alpha olefin.

4. The method of claim 1, wherein the comparison phase angle is about 5 to about 85°.

5. The method of claim 1, wherein the comparison phase angle is about 20 to about 60°.

6. The method of claim 1, wherein the comparison phase angle is about 30 to about 40°.

7. The method of claim 1, wherein two or more of the sample complex moduli are measured simultaneously.

8. The method of claim 1, wherein the creating an array of the copolymer samples step includes extruding a copolymer sample in a molten state, followed by pressing and forming the copolymer sample into a flat disk.

9. The method of claim 1, wherein the creating an array of the copolymer samples step includes combining a copolymer sample with a solvent, depositing at least a portion of the combined copolymer sample and the solvent on a surface, removing at least a portion of the solvent, followed by pressing and forming the copolymer sample into a flat disk.

10. A high throughput method to determine an amount of a comonomer in a copolymer sample, the method comprising the steps of:
    a) providing a plurality of copolymer samples;
    b) creating an array of the copolymer samples;
    c) measuring a sample crossover modulus of each of the copolymer samples at a comparison phase angle;
    d) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

11. The method of claim 10, wherein the step of providing a plurality of copolymer samples comprises providing a plurality of copolymers comprising ethylene, propylene, or both ethylene and propylene.

12. The method of claim 10, wherein the copolymer samples comprise a $C_4$ to $C_{40}$ alpha olefin.

13. The method of claim 10, wherein the comparison phase angle is about 5 to about 85°.

14. The method of claim 10, wherein the comparison phase angle is about 20 to about 60°.

15. The method of claim 10, wherein the comparison phase angle is about 30 to about 40°.

16. The method of claim 10, wherein two or more of the sample crossover moduli are measured simultaneously.

17. The method of claim 10, wherein the creating an array of the copolymer samples step includes extruding a copolymer sample in a molten state, followed by pressing and forming the copolymer sample into a flat disk.

18. The method of claim 10, wherein the creating an array of the copolymer samples step includes combining a copolymer sample with a solvent, depositing at least a portion of the combined copolymer sample and the solvent on a surface, removing at least a portion of the solvent, followed by pressing and forming the copolymer sample into a flat disk.

19. A method to determine an amount of a comonomer in a copolymer sample, the method comprising the steps of:
    a) providing a copolymer sample;
    b) measuring a sample crossover modulus of the copolymer sample at a comparison phase angle;
    c) determining the amount of a comonomer in the copolymer sample by comparing the sample crossover modulus to a calibration curve, wherein the calibration curve relates a concentration of the comonomer in the copolymer sample to a crossover moduli of the copolymer sample determined at the comparison phase angle.

20. The method of claim 19, wherein the copolymer sample comprises ethylene, propylene, or both ethylene and propylene.

21. The method of claim 19, wherein the copolymer sample comprise a $C_4$ to $C_{40}$ alpha olefin.

22. The method of claim 19, wherein the comparison phase angle is about 5 to about 85°.

23. The method of claim 19, wherein the comparison phase angle is about 20 to about 60°.

24. The method of claim 19, wherein the comparison phase angle is about 30 to about 40°.

25. The method of claim 19, wherein the providing a copolymer sample step includes extruding the copolymer sample in a molten state, followed by pressing and forming the copolymer sample into a flat disk.

26. The method of claim 19, wherein the providing a copolymer sample step includes combining a copolymer sample with a solvent, depositing at least a portion of the combined copolymer sample and the solvent on a surface, removing at least a portion of the solvent, followed by pressing and forming the copolymer sample into a flat disk.

* * * * *